United States Patent
Chandy et al.

(10) Patent No.: US 7,235,577 B1
(45) Date of Patent: Jun. 26, 2007

(54) NON-PEPTIDE INHIBITION OF T-LYMPHOCYTE ACTIVATION AND THERAPIES RELATED THERETO

(75) Inventors: K. George Chandy, Laguna Beach, CA (US); Heike Wulff, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/402,532

(22) Filed: Mar. 28, 2003

Related U.S. Application Data

(62) Division of application No. 09/479,391, filed on Jan. 6, 2000, now Pat. No. 6,803,375.

(51) Int. Cl.
*A61K 31/415* (2006.01)

(52) U.S. Cl. ..................................................... 514/406
(58) Field of Classification Search ...................... None
See application file for complete search history.

(56) References Cited

U.S. PATENT DOCUMENTS 6,028,103 A * 2/2000 Brugnara et al. ........... 514/492
6,545,028 B2 * 4/2003 Jensen et al. ............... 514/356

FOREIGN PATENT DOCUMENTS

| WO | WO 97/34589 | * | 9/1997 |
| WO | WO 99/25347 | * | 5/1999 |
| WO | WO 00/69439 |   | 11/2000 |

OTHER PUBLICATIONS

Wulff, H., et al. Proc. Natl. Acad. Sci. USA 2000 97, 8151-8156.*
Cahalan, M. D., et al. Curr. Opinion Biotech. 1997, 8, 749-756.*
Forgue-Lafitte, M.-E., et al. Cancer Research 1992, 52, 6827-6831.*
Jensen, B. S., et al. Proc. Natl. Acad. Sci. USA 1999, 96, 10917-10921.*
Dunn, P. M. J. Membrane Biol. 1998, 165, 133-143.*
Brugana, C., et al. J. Clin. Invest. 1996, 97, 1227-1234.*
Aussel, C., et al. Cellular Immunol. 1994, 155, 436-445.*
Aussel, C., et al. FEBS 1993, 319, 155-158.*
Wulff, H., et al. J. Biol. Chem. 2001, 276, 32040-32045.*
Alvarez, Javier, Montero, Mayte, and Garcia-Sancho, Javier, High Affinity Inhibition of Ca2+-dependent K+ Channels by Cytochrome P-450 Inhibitors, the Journal of Biological Chemistry, Nov. 7, 1999, pp. 11789-11793, vol. 297, No. 17.
Aussel, Claude and Breittmayer, Jean-Philippe, Imidazole antimycotics inhibitors of cytochrome P450 increase phosphtidylserine synthesis similarly to K+-channel blockers in Jurkat T cells, Federation of European Biochemical Societies, Mar. 1993, pp. 155-158, vol. 319, No. 1.2, Published Elsevier Science Publishers B.V.
Aussel, Claude, Briettmayer, Jean Philippe, Ticchioni, Michel, Pelassy, Claudette, and Bernard, Alain, Regulation of T Cell Activation by Cytochrome P450 Inhibitors, 1994, pp. 436-445.
Breittmayer, Jean-Philippe, Berthe, Pascal, Cousin, Jean-Louis, Bernard, Alain and Aussel, Claude, CD3 Monoclonal Antibodies Evoke the Same Cytochrome P450-Regulated Capacitative Entry of Calcium as Thapsigargin in Jurkat T Cells, Apr. 22, 1993, pp. 143-151, Cellular Immunology, vol. 52.
Gow, P.J., Corrigall, V. and Panayi, G.S., The Effect of Clotrimazole on Human Lymphocyte Responsiveness to Plant Mitogens,, Department of Medicine, Arthritis Research Unit, Guy's Hospital MEdicla School, Feb. 3, 1978, pp. 543-548, London SE 1 9RT.
Forgue-Lafitte, Marie-Elisabeth, Coudray, Anne-Marie, Fagot, Dominique and Mester, Jan, Effects of Ketoconazole on the Proliferation and Cell Cycel of Human Cancer Cell Lines, Cancer Research, Dec. 15, 1992, vol. 52, pp. 6827-6831, Published Paris, France.
Fulton, David, McGiff, John C. & Quilley, John, Role of K+ channels in the vasodilator response to bradykinin in the rat heart, Br. J. Pharmacol, 1994, pp. 954-958, vol. 113, New York.
Gordon, D., Nouri, A.M.E. & Thomas, R.U., Selective Inhibitionof Thromboxane Biosynthesis in Human Blood Mononuclear Cells and the Effects on Mitgoen-Stimulate Lymphocyte Proliferation, Br.J. Pharmac, 1981, pp. 469-475, vol. 74, London, England.
Miller, J.J., Reeves, S.C. & Salaman, J.R., Effects of Simple Imidazoles on Human Peripheral Blood Lymphocytes Stimulated by Mitogen or Allogenic Cells, J. of Immunopharmacology, 1980, pp. 225-243, vol. 2, Issue No. 2.
Stuart, J., Mojiminiyi, F.B.O., Stone, P.C.W., Culliford, SLJ. and Ellory, J.C., Additive in vitro effects of anti-sickling drugs, British Journal of Haematology, 1994, pp. 820-823, vol. 86.
Vuddhakul, V., McCormack, J.G., Seow, W.K. and Thong, Y.H., Effects of the newer antifungal agents (Bifonazole, ICI 195, 739 and Amorolfin) on in vitro phagocytic lymphocytic and natural-killer cell responses, Int.l J. Immunopharmacology, 1989, pp. 817-828, vol. 11, No. 7, Great Britain.
Chandy, K. George, Cahalan, Michael, Pennington, Michael, Norton, Raymond S., Wulff, Heike, Gutman, George A., Potassium channels in T lymphocytes: toxins to therapeutic immunosuppresants, Toxicon, 2001, pp. 1269-1276, vol. 39, Elsevier.

(Continued)

Primary Examiner—Sreenivasan Padmanabhan
Assistant Examiner—Kevin Capps
(74) Attorney, Agent, or Firm—Robert D. Buyan; Stout, Uxa, Buyan & Mullins

(57) ABSTRACT

Compounds, preparations and methods for immunosuppressive treatment of autoimmune disorders, graft rejection and/or graft/host disease. Therapeutically effective amounts of certain substituted triarylmethane compounds, such as 1-[(2-chlorophenyl)diphenylmethyl]-1H-pyrazole, are administered to mammalian patients to selectively inhibit the calcium-activated $K^+$ channel (IKCa1) in lymphocytes, monocytes, macrophages, platelets or endothelial cells without concomitant inhibition of P450-dependent enzyme systems, resulting in reduction of antigen-, cytokine-, or mitogen-induced calcium entry through store operated calcium channels in these cells, suppression of cytokine production by these cells, and inhibition of activation of these cells. Such inhibition of the $Ca^{++}$ activated $K^+$ channel (IKCa1) prevents the pre-$Ca^{++}$ stage of cell activation and thus causes immunosuppression and an anti-inflammatory response.

8 Claims, 5 Drawing Sheets

OTHER PUBLICATIONS

Cahalan, Michael D., Wulff, Heike, and Chandy, K. George, Molecular Properties and Physiological Roles of Ion Channels in the Immune System, Journal of Clinical Immunology, 2001, pp. 235-252, vol. 21, No. 4, Planium Publishing Coporation.

Wulff, Heike, Gutman, George A., Cahalan, Michael D., and Chandy, K. George, Delineation of the Clotrimazole/TRAM-34-Binding Site on the Intermediate Conductance Calcium-activated Potassium Channel, IKCal, The Journal of Biological Chemistry, 2001, pp. 32040-32045, vol. 276, No. 34, The American Society for Biochemistry and Molecular Biology, Inc.

Ghanshani, Sanjiv, Wulff, Heike, Miller, Mark J., Rohm, Heike, Neben, Amber, Gutman, George A., Cahalan, Michael D., and Chandy, K. George, Up-regulation of the IKCal Potassium Channel during T-cell Activation, The Journal of Biological Chemistry, 2000, pp. 37137-37149, vol. 275, No. 47, The American Society for Biochemistry and Molecular Biology, Inc.

Wulff, Heike, Miller, Mark J., Hansel, Wolfram, Grissmer, Stephan, Cahalan, Michael D., Chandy, K. George, Design of a potent and selective inhibitor of the intermediate-conductance Ca2+-activated K+ channel, IKCa1: A potential immunosuppressant, PNAS, Jul. 5, 2000, pp. 8151-8156, vol. 97, No. 14.

Rajesh Kanna, martin C. Chang, William J. Joiners, Leonard K. Kaczmarck, and Lyanne C. Schlichter, hSK4/hIK1, a Calmodulin-binding $K_{ca}$ Channel in Human T Lymphocytes; Mar. 12, 1999; *The Journal of Biological Chemistry*; pp. 14838-14849.

Bo Skaaning Jensen, Niels Odum, Nanna Koschmieder Jorgensen, Palle Christophersen, and Soren-Peter Olesen; Inhibition of T Cell Proliferation by Selective Block of Ca2+-activated K+ Channels; Mar. 26, 1999; *Proc. Natl. Acad. Sci. USA*: 10917-10921.

* cited by examiner

NON-PEPTIDE INHIBITION OF T-LYMPHOCYTE ACTIVATION AND THERAPIES RELATED THERETO

RELATED APPLICATION

This patent application is a division of U.S. patent application Ser. No. 09/479,391 filed on Jan. 6, 2000, which issued as U.S. Pat. No. 6,803,375 on Oct. 12, 2004.

FIELD OF THE INVENTION

This invention relates generally to chemical compositions, preparations and methods for medical treatment and more particularly to the use of certain substituted triarylmethane compounds for immunosuppressive treatment of autoimmune disorders or inflammatory diseases, or the treatment or prevention of transplant rejection or graft-versus-host disease in mammalian patients.

BACKGROUND OF THE INVENTION

Organ transplantation has become routine in many parts of the world. Transplants of liver, kidney, heart, lung and pancreas, are now regularly performed as treatment for end-stage organ disease. The outcomes of organ transplant procedures have progressively improved with the development of refinements in tissue typing, surgical techniques, and more effective immunosuppressive treatments. However, rejection of transplanted organs remains a major problem. T-lymphocytes play a central role in the immune response and they are responsible, in large measure, for the rejection of many transplanted organs. They are also responsible for the so-called graft-versus host disease in which transplanted bone marrow cells recognize and destroy MHC-mismatched host tissues. Accordingly, drugs such as cyclosporin and FK506 that suppress T-cell immunity are used to prevent transplant rejection and graft-versus-host disease. Unfortunately, these T-cell inhibiting drugs are toxic, with liver and renal toxicities limiting their use.

Autoimmune diseases encompass a whole spectrum of clinical disorders wherein a patient's immune system mistakenly attacks self, targeting the cells, tissues, and organs of the patient's own body. The following are some examples of autoimmune diseases, categorized with respect to the target organ that is principally affected by each such disease:

| Nervous System: | Gastrointestinal Tract: |
|---|---|
| Multiple sclerosis | Crohn's Disease |
| Myasthenia gravis | Ulcerative colitis |
| Autoimmune neuropathies such as Guillain-Barré | Primary biliary cirrhosis |
| | Autoimmune hepatitis |
| Autoimmune uveitis | Endocrine: |
| Blood: | Type 1 diabetes mellitus |
| Autoimmune hemolytic anemia | Addison's Disease |
| Pernicious anemia | Grave's Disease |
| Autoimmune thrombocytopenia | Hashimoto's thyroiditis |
| Vascular: | Autoimmune oophoritis and |
| Temporal arteritis | orchitis |
| Anti-phospholipid syndrome | Multiple Organs and/or |
| Vasculitides such as | Musculoskeletal System: |
| Wegener's granulomatosis | Rheumatoid arthritis |
| Behcet's disease | Systemic lupus erythematosus |
| Skin: | Scleroderma |
| Psoriasis | Polymyositis, dermatomyositis |
| Dermatitis herpetiformis | Spondyloarthropathies such as |
| Pemphigus vulgaris | ankylosing spondylitis |
| Vitiligo | Sjogren's syndrome |

Irrespective of the particular organ(s) affected, T-lymphocytes are believed to contribute to the development of autoimmune diseases. The currently available therapies for these diseases are largely unsatisfactory and typically involve the use of glucocorticoids (e.g. methylprednisolone, prednisone), non-steroidal anti-inflammatory agents, gold salts, methotrexate, antimalarials, and other immunosuppressants such as cyclosporin and FK-506.

Thus, the search for additional immunosuppressive agents for preventing transplant rejection and for the treatment of autoimmune and inflammatory disorders occupies considerable attention in the pharmaceutical industry. Since cytokines such as interferon-gamma and tumor necrosis factor-alpha play a critical role in transplant rejection and in the pathophysiology of autoimmune disorders, much effort has been invested in the development of agents that suppress their production, secretion and/or end-organ effect.

There is an excellent track record of treating nervous and cardiovascular disorders with ion channel modulators—either openers or blockers. Ion channel blockers as a general class, represent the major therapeutic agents for treatment of stroke, epilepsy and arrhythmias. Since ion channels play a major role in the T-cell immune response, these channels may represent attractive targets for pharmaceutical immunomodulation.

The early stages of T-cell activation may be conceptually separated into pre-$Ca^{++}$ and post-$Ca^{++}$ events (Cahalan and Chandy 1997, Curr. Opin. Biotechnol. 8: 749). Following engagement of antigen with the T-cell antigen-receptor, activation of tyrosine kinases and the generation of inositol 1,4,5-triphosphate leads to the influx of $Ca^{++}$ through store-operated calcium channels (also known as Calcium-Release Activated Calcium or CRAC channels) and the rise of cytoplasmic $Ca^{++}$ concentration (Cahalan and Chandy 1997, Curr. Opin. Biotechnol. 8: 749; Kerschbaum and Cahalan 1999, Science 283: 836; Kerschbaum and Cahalan 1998; J. Gen. Physiol. 111: 521). The rise in $Ca^{++}$ activates the phosphatase calcineurin, which then dephosphorylates a cytoplasmically localized transcription factor (N-FAT) enabling it to accumulate in the nucleus and bind to a promoter element of the interleukin-2 gene. Along with parallel events involving the activation of protein kinase C and ras, gene transcription leads to lymphokine secretion and to lymphocyte proliferation. Some genes require long-lasting $Ca^{++}$ signals while others require only a transient rise of $Ca^{++}$. Furthermore, $Ca^{++}$ immobilization of the T-cell at the site of antigen presentation helps to cement the interaction between T-cell and the antigen-presenting cell and thereby facilitate local signaling between the cells (Negulescu 1996, Immunity 4:421).

Ion channels underlie the $Ca^{++}$ signal of T-lymphocytes. $Ca^{++}$ ions move across the plasma membrane through a channel termed the store-operated $Ca^{++}$ channel or the CRAC channel which is activated by depletion of internal calcium stores like the endoplasmic reticulum (Cahalan and Chandy 1997, Curr. Opin. Biotechnol. 8: 749). Two distinct types of potassium channels indirectly determine the driving force of calcium entry through the store-operated $Ca^{2+}$ channel (Cahalan and Chandy 1997, *Curr. Opin. Biotechnol.* 8: 749). The first is the voltage-gated Kv1.3 channel (Cahalan 1985, *J. Physiol.* 385: 197; Grissmer 1990, *Proc. Natl. Acad. Sci. USA* 87: 9411; Verheugen 1995, *J. Gen. Physiol.* 105: 765; Aiyar 1996, *J. Biol. Chem.* 271: 31013; Cahalan and Chandy 1997, *Curr. Opin. Biotechnol.* 8: 749) and the second is the intermediate-conductance calcium-activated potassium channel, IKCa1 (Grissmer 1993, *J. Gen. Physiol.* 102: 601; Fanger 1999 *J. Biol. Chem.* 274: 5746; Rauer 1999, *J. Biol. Chem.* 274: 21885) which is also known as IK1 (VanDorpe 1998, *J. Biol. Chem.* 273: 21542), hSK4 (Joiner 1997, *Proc. Natl. Acad. Sci. USA* 94: 11013; Khanna 1999, *J. Biol. Chem.* 274: 14838) and hKCa4 (Lodgson 1997, *J. Biol. Chem.* 272: 32723; Ghanshani 1998, *Genomics* 51: 160). When these potassium channels open, the resulting efflux of $K^+$ hyperpolarizes the membrane, which in turn accentuates the entry of $Ca^{++}$, which is absolutely required for downstream activation events (Cahalan and Chandy 1997, *Curr. Opin. Biotechnol.* 8: 749). Blockers of the Kv1.3 and IKCa1 channels suppress human T-cell activation, when applied independently, and produce greater suppression when applied together (DeCoursey 1984, *Nature* 307: 465; Chandy *J. Exp. Med.* 160: 369; Koo 1997, *J. Immunol.* 158: 5120; Nguyen 1995, *Mol. Pharmacol.* 50: 1672; Hanson 1999, *Br. J. Pharmacol.* 126:1707; Kalman 1998, *J. Biol. Chem.* 278: 32697; Khanna 1999, *J. Biol. Chem.* 274: 14838; Jensen 1999; *Proc. Natl. Acad. Sci. USA* 96: 10917). One mechanism for the immunosuppression by $K^+$ channel blockers is via membrane depolarization, which reduces $Ca^{++}$ entry through CRAC channels in the T-cell membrane, which in turn leads to suppression of calcium-dependent signaling events during human T-cell activation (Cahalan and Chandy 1997, *Curr. Opin. Biotechnol.* 8: 749; Koo 1999, *Cell. Immunol.* 197: 99).

Clotrimazole, a non-selective inhibitor of IKCa1, suppresses mitogen-stimulated T-cell activation, especially of pre-activated cells (Khanna 1999, *J. Biol. Chem.* 274: 14838; Jensen 1999, *Proc. Natl. Acad. Sci. USA* 96: 10917). Clotrimazole and related imidazoles, other than the compounds of this invention, have also previously been described for use in treating rheumatoid arthritis, an autoimmune disorder (Wojtulewski 1980, *Ann. Rheum. Dis.* 39: 469; Wyburn-Mason 1976, U.S. Pat. No. 4,073,922; Wyburn-Mason 1987, U.S. Pat. No. 183,941; Wyburn-Mason 1979, U.S. Pat. No. 4,218,449). However, clotrimazole shows considerable toxicity with increasing doses, toxicity being primarily associated with its potent (nanomolar) inhibition of cytochrome P450 enzymes (Wojtulewski 1980, *Ann. Rheum. Dis.* 39: 469; Burgess 1972 *Antimicrob. Agents Chemother.* 2: 423; Brugnara 1996, *J. Clin Invest* 97: 1227). Thus, there clearly is a need for newer analogs that block IKCa1 without concomitant inhibition of cytochrome P450-dependent enzymes.

Other patents have described the use of clotrimazole, related azole antimycotics (e.g., miconazole and econazole) and related aromatic halides for the treatment of cancer (Halperin 1994, WO 96/08240; Halperin 1997 U.S. Pat. No. 5,633,274), but only at micromolar concentrations (Benzaquen 1995, *Nat. Med.* 1: 534), substantially greater than the concentrations required to block the IKCa1 channel (~20–100 nM), suggesting that the mechanism of suppression of proliferation might be unrelated to channel block. Also at micromolar concentrations, clotrimazole, related azole antimycotics (e.g., miconazole and econazole) and related aromatic halides have been described for use in the treatment of arteriosclerosis as a hyperproliferative disease (Halperin 1994, WO 94/189680 and U.S. Pat. No. 5,358,959), and for the treatment of diseases characterized by neovascularization (Halperin 1996, U.S. Pat. No. 5,512,591; Halperin 1997, U.S. Pat. No. 5,643,936 and U.S. Pat. No. 5,591,763).

At least some of the triarylmethyl-1H-pyrazole compounds of the present invention have also previously been described in PCT International Publication WO 97/34599 entitled USE OF CLOTRIMAZOLE AND RELATED COMPOUNDS IN THE TREATMENT OF DIARRHEA, as being useable for the treatment of diarrhea, although they do not constitute preferred embodiments of the inventions.

Also, PCT International Publication WO/97/34589 entitled TRIARYL METHANE COMPOUNDS FOR SICKLE CELL DISEASE describes various substituted triarylmethane compounds as effective treatments for sickle cell disease due to their ability to inhibit ion flux through the calcium activated potassium channel (Gardos channel) of erythrocytes, which has now been shown to be encoded by the IKCa1 gene (VanDorpe 1998, *J. Biol. Chem.* 273: 21542). Clotrimazole, the preferred compound in this invention is in phase II trials for the treatment of sickle cell disease gene (VanDorpe 1998, *J. Biol. Chem.* 273: 21542), but at higher doses causes toxic side effects most likely due to its inhibition of cytochrome P450 enzymes. The PCT International Publication WO/97/34589 also describes various substituted triarylmethane compounds as effective treatments for diseases characterized by unwanted or abnormal cell proliferation (the examples cited being melanoma cells and fibroblast proliferation), but at only micromolar concentrations (Benzaquen 1995, *Nat. Med.* 1: 534; Halperin 1997 U.S. Pat. No. 5,633,274; PCT application WO97/34589; PCT application WO/97/08240) which are substantially higher than that required for block of the IKCa1 channel (half-block at 20–100 nM), suggesting that the mechanism of suppression of cell proliferation might be unrelated to channel block. Furthermore, since the three compounds used to support this claim, clotrimazole, ketoconazole and miconazole (Benzaquen 1995, *Nat. Med.* 1: 534) also inhibit cytochrome P450 enzymes at nanomolar concentrations (Mason 1987, *Steroids* 50: 179; Morris 1992, *FASEB J.* 6: 752), the mechanism of suppression of abnormal proliferation may be related to inhibition of these enzymes. Another possible mechanism for suppression of proliferation stated in PCT application WO/97/34589 is non-specific cytotoxicity. Therefore, the claims in PCT application WO/97/34589 that suppression of abnormal proliferation is due solely to alteration of transmembrane ion fluxes cannot be substantiated.

WO 97/34589 does not describe or suggest that the substituted triarylmethane compounds disclosed therein are capable of selectively blocking the calcium activated potassium channels encoded by the IKCa1 gene in resting and activated T-lymphocytes, or that such compounds would, alone or in combination with other inhibitors of T-cell signaling cascades, suppress antigen-, cytokine- and/or mitogen-stimulated calcium-entry through store-operated calcium channels, and/or cytokine production and/or activation of human T-lymphocytes, without concomitant inhibition of cytochrome P450 enzymes, leading to immunosuppressive activity when administered to mammalian patients.

Given the shortcomings associated with the currently available modes of therapy for autoimmune disorders, transplant rejection and graft-versus-host disease, there remains a need for the development of new immunosuppressive drugs that are capable of selectively inhibiting the activation of lymphocytes with minimal side effects, and without affecting the cytochrome P450 enzyme system.

SUMMARY OF THE INVENTION

The present invention generally comprises pharmaceutical preparations containing substituted triarylmethane compounds, as listed in Appendix A, and methods for immunosuppressive treatment of autoimmune disorders, graft rejection and/or graft-versus-host disease by administering therapeutically effective amounts of such compounds to mammalian patients.

In accordance with the invention, there is provided a method for inhibiting antigen-, cytokine-, or mitogen-induced calcium-entry through store-operated calcium channels, cytokine production and cell activation in lymphocytes, monocytes, macrophages and for treating autoimmune disorders, graft rejection and/or graft-versus-host disease by administering to a mammalian patient a therapeutically effective amount of at least one compound having the general structural formula:

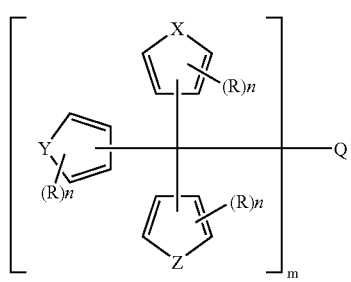

Formula I

Wherein,

X, Y and Z are same or different and are independently selected from $CH_2$, O, S, $NR_1$, $N=CH$, $CH=N$ and $R_2-C=C-R_3$, where $R_2$ and $R_3$ are H or may combine to form a saturated or unsaturated carbocyclic or heterocyclic ring, optionally substituted with one or more R groups;

$R_1$ is selected from H, alkyl, alkenyl, alkynyl, cycloalkyl, aryl, acyl and aroyl, optionally substituted with hydroxy, amino, substituted amino, cyano, alkoxy, halogen, trihaloalkyl, nitro, thio, alkylthio, carboxy and alkoxycarbonyl groups;

R is selected from H, halogen, trihaloalkyl, hydroxy, acyloxy, alkoxy, alkenyloxy, thio, alkylthio, nitro, cyano, ureido, acyl, carboxy, alkoxycarbonyl, $N-(R_4)(R_5)$ and saturated or unsaturated, chiral or achiral, cyclic or acyclic, straight or branched hydrocarbyl group with from 1 to 20 carbon atoms, optionally substituted with hydroxy, halogen, trihaloalkyl, alkylthio, alkoxy, carboxy, alkoxycarbonyl, oxoalkyl, cyano and $N-(R_4)(R_5)$ group, $R_4$ and $R_5$ are selected from H, alkyl, alkenyl, alkynyl, cycloalkyl and acyl or $R_4$ and $R_5$ may combine to form a ring, wherein a carbon may be optionally substituted by a heteroatom selected from O, S or $N-R_6$, $R_6$ is H, alkyl, alkenyl, alkynyl, cycloalkyl, hydroxyalkyl or carboxyalkyl, n is 0–5; m is 1 or 2; with the proviso that when m is 1, Q is selected from OH, CN, carboxyalkyl, $N-(R_7)(R_8)$, where $R_7$ and $R_8$ are selected from H, lower alkyl (1–4C), cycloalkyl, aryl, acyl, amido, or $R_7$ and $R_8$ may combine to form a saturated or unsaturated heterocylic ring and optionally substituted with up to 3 additional heteroatoms selected from N, O, and S; or —NH-heterocycle, where the heterocycle is represented by thiazole, oxazole, isoxazole, pyridine, pyrimidine, and purine and where U and V are selected from H and O; and

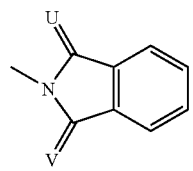

when m is 2, Q is a spacer of from 2–10 carbons either as a straight or branched hydrocarbon chain, or containing a hydrocarbon ring such as phenyl.

In the most preferred embodiment of this invention, X, Y, and Z are $R_2-C=C-R_3$, where $R_2$ and $R_3$ are H; R is selected from H and halogen, preferably, F and Cl;

m is 1; and

Q is $-N-(R_7)(R_8)$, where $R_7$ and $R_8$ are selected from H, acyl, amido, and $R_7$ and $R_8$ combine to form a saturated or unsaturated heterocyclic ring, optionally substituted with up to three heteroatoms selected from N, O, or S, for example, pyrrolidine, piperidine, pyrazole, oxazole, isoxazole, tetrazole, azepine, etc., which may be optionally substituted with a lower alkyl or amino group.

Further in accordance with the invention, preferred compounds of this invention having the general Formula I above, are a group of triarylmethyl-1H-pyrazole compounds that have structural Formula I-A below:

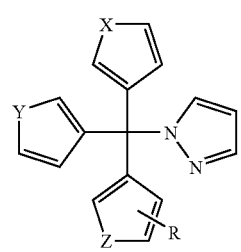

Formula 1-A

Wherein:

X, Y, and Z are $R_2-C=C-R_3$, where $R_2$ and $R_3$ are H;

R is selected from H and halogen, preferably, F and Cl;

Compounds of Formula I-A have been determined to selectively inhibit the intermediate-conductance calcium-activated potassium channel, IKCa1, at low nanomolar concentrations, and exhibit 200–1500 fold selectivity for this channel over other ion channels, and over cytochrome P450-dependent enzymes.

Still further in accordance with the invention, 1-[(2-chlorophenyl)diphenyl methyl]-1H-pyrazole (designated as T34 in Appendix A) and possibly other compounds of Formulas I and I-A above, when administered to mammalian patients, inhibit (i.e., block or partially block) the intermediate conductance $Ca^{++}$ activated K channel (IKCa1)

expressed in resting and activated lymphocytes, monocytes, macrophages, platelets and endothelial cells. By inhibiting the IKCa1 channel in lymphocytes, monocytes, macrophages, platelets and endothelial cells the present invention prevents or deters $Ca^{++}$ entry and, thus, disrupts the signaling cascade that leads to cytokine production and cell activation. It is by this mechanism, and possibly others, that the compounds of Formulas I and I-A are useable to cause suppression of immune and anti-inflammatory responses. Unlike clotrimazole, the compounds of Formula I and I-A lack the imidazole moiety that is believed to be responsible for inhibition of cytochrome P450-dependent enzymes and, thus, the compounds of Formula II above will inhibit or block the $Ca^{++}$ activated $K^+$ channel (IKCa1) without also causing inhibition of cytochrome P450-dependent enzymes. In this manner, the compounds of Formula I and I-A can be administered in amounts that are effective to inhibit (i.e., block or partially block) the $Ca^{++}$ activated $K^+$ channel (IKCa1) without causing at least some of the toxic side-effects associated with cytochrome P450 inhibition by clotrimazole.

DETAILED DESCRIPTION OF CERTAIN EMBODIMENTS OF THE INVENTION

Figure 1A:
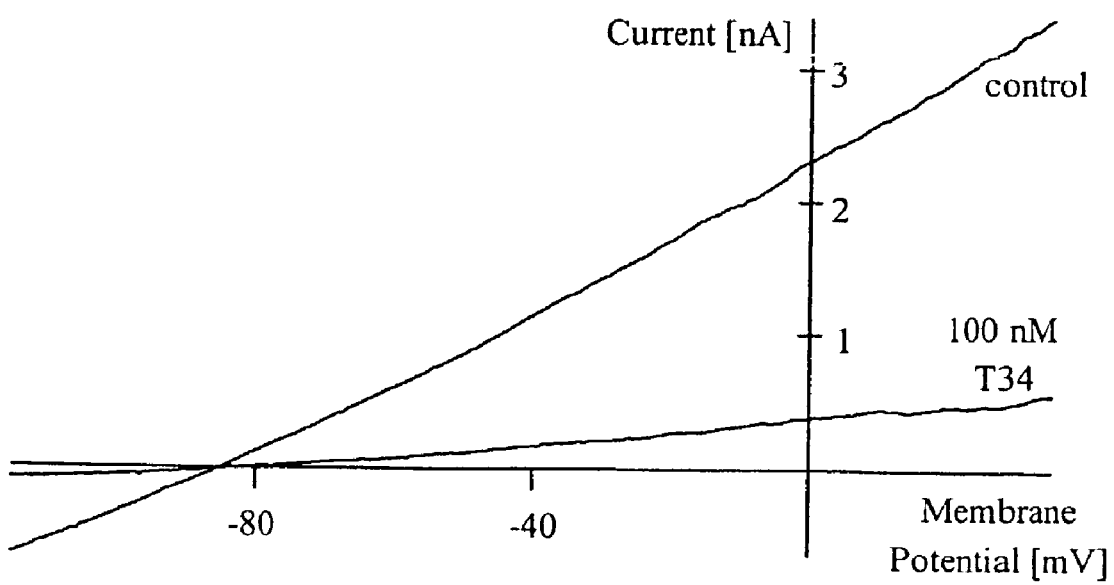
FIG. 1a shows the block of an IKCa1 current (hIKCa1 expressed in COS-7 cells) by 100 nM T34.

The following detailed description, and the examples contained therein, are provided for the purpose of describing and illustrating certain embodiments of the invention only and are not intended to limit the scope of the invention in any way.

The present invention provides for the use of therapeutically effective substituted triaryl methane compounds that are more selective in inhibiting the said channel in nanomolar concentrations and exhibiting no inhibitory effect on the cytochrome P450-dependent enzyme systems at 50 times greater concentrations. Because the imidazole moiety is responsible for inhibition of cytochrome P-450-dependent enzymes, applicants have synthesized compounds of Formula I and I-A above that do not include the imidazole moiety, including instead other heterocyclic groups. Applicants have also synthesized a range of triaryl-methanols, amines, ureas, acetonitriles and related compounds, as listed in Appendix A, by synthetic methodologies outlined in Scheme 1 below. The triarylmethyl-1-H-pyrazoles of this invention potently block IKCa1. Applicants have further discovered that one particular compound of this invention having Structural formula I-B below, exhibits ~3-fold greater affinity for the channel ($K_d$=20 nM) than clotrimazole ($K_d$=70 nM), and does not inhibit cytochrome P450 3A4, the major xenobiotic metabolizing enzyme in the human liver, even at a concentration of 10 μM. Four other compounds in this series (T39, T40, T46 and T84) are more potent inhibitors of IKCa1 channels than clotrimazole (TABLE 8).

Furthermore, applicants have discovered that the ratio of cytochrome P-450-dependent enzyme systems inhibition ($EC_{50}$) to IKCa1 inhibition ($K_d$) needs to be >50–100 to achieve the therapeutic effect for prevention of the diseases modulated by IKCa1 channel without the aforementioned side effects evident in clotrimazole and related imidazoles.

As a further test of selectivity, applicants have evaluated 1-[(2-chlorophenyl)diphenylmethyl]-1H-pyrazole, one of the compounds of this invention (designated as T-34 in Appendix A), on other cloned and native ion channels, (Kv1.1–1.5, Kv3.1, Kv4.2, Jurkat-$SK_{Ca}$, BKCa, hSKM1-Na, CRAC and lymphocyte chloride channels). All of these channels were blocked with $K_d$ values~5 μM. Thus, T34 was found to be a remarkably potent and selective IKCa1 inhibitor. Because of its structural similarity to clotrimazole and based on experimental data described in the examples below, we expect that T34 (logP=4.0 versus 3.5 for clotrimazole) will have a similar or slightly better bioavailabity than clotrimzole and, contrary to clotrimazole, no side effects mediated by inhibition of cytochrome P450-dependant enzymes.

The invention is particularly concerned with compounds for effective treatments for auto-immune disorders, transplant rejection, inflammatory disorders and graft-versus-host disease. Accordingly, the present invention provides compositions and methods suitable for treatment of said diseases, and further provides therapy devoid of side effects associated with currently available drugs on the market.

The present invention includes methods that are specifically intended to suppress the immune system and reduce inflammation in a mammalian patient who is in need of such treatment. Specifically, the method of this invention is useful in treating and preventing the resistance to transplantation rejection of organs or tissues (such as heart, kidney, liver, lung, bone marrow, cornea, pancreas, limb, nerves, medulla ossium, duodenum, small bowel, skin, pancreatic islet etc. including xeno transplantation), graft-versus-host diseases, autoimmune diseases such as rheumatoid arthritis, systemic lupus erythematosis, Hashimoto's thyroiditis, multiple sclerosis, myasthenia gravis, type I diabetes mellitus, nephrotic syndrome, steroid-dependent and steroid-resistant nephrosis, palmar-plantar pustolosis, allergic encephalomyelitis, glomerulonephritis, Behcet's syndrome, ankylosing spondylitis, polymyositis, fibromyositis, etc.

The compounds of this invention are also useful for treating inflammatory, proliferative and hyperproliferative skin diseases and cutaneous manifestations of immunologically mediated illnesses such as psoriasis, psoriatic arthritis, atopic dermatitis, contact dermatitis and other eczematous dermatitises, seborrhoic dermatitis, Lichen planus, Pemphigus, bullous Pemphigus, Epidermolysis bullosa, angiodemas, vasculilides, erythemas, cutanous eosinophilias, acne, Alopecia greata, and arteriosclerosis.

The compounds of the invention are further useful in the treatment of respiratory diseases, for example sarcoidosis, fibroid lung, idiopathic interstitial pneumonia, and reversible obstructive airway diseases, including conditions such as asthma, including bronchial asthma, allergic asthma, intrinsic asthma, extrinsic asthma and dust asthma, bronchitis and the like.

The compounds may also be useful for the treating hepatic injury associated with ischemia.

The compounds may also be indicated in certain eye diseases such as keratoconjunctivitis, vernal conjunctivitis, keratitis, uveitis, corneal leukoma, occular pemphigus, Mooren's ulcer, Scleritis, Graves' ophtalmopathy, sympathetic ophthalmia and the like.

The compounds are also useful treating inflammatory bowel diseases (e.g. Crohn's disease), neurological diseases (including Guillain-Barre syndrome, Meniere's disease, radiculopathy), endocrine diseases (including hyperthyroidism and Basedow's disease), hematological diseases (including pure red cell aplasia, aplastic anemia, hypoplastic anemia, idiopathic thrombocytopenic purpura, autoimmune hemolytic anemia, agranulocytosis and anerythroplasia), bone diseases (including osteoporosis), respiratory disease (including sarcoidosis, idiopathic interstitial pneumonia), skin diseases (including dermatomyositis, leukoderma vulgaris, ichthyosis vulgaris, photoallergic sensitivity and cutanous T cell lymphoma), genitals (orchiitis, vulvitis), circulatory diseases (including arteriosclerosis, polyarteritis nodosa, vasculitis, Buerger's disease, and myocardosis), collagen disorders (including scleroderma, aortitis syndrome, eosinophilic fascitis, Wegener's granulomatosis, Sjogren's syndrome, periodontal diseases), kidney diseases (including nephrotic syndrome, hemolytic-uremic syndrome, Goodpasture's syndrome) and muscular dystrophy. The compounds may also be useful for the treatment of diseases including intestinal inflammations/allergies such as Coeliac disease, proctitis, ulcerative colitis, eosinophilic gastroenteritis, mastocytosis, Crohn's disease and ulcerative colitis and food-related allergic diseases which have symptomatic manifestations remote from the gastrointestinal tract, for example migraine, rhinitis and eczema. Further, the invention can be used for treating preventing or treating inflammation of mucosa or blood vessels (such as leukotriene-mediated diseases), gastric ulcers, vascular damage caused by ischemic diseases and thrombosis, ischemic bowel diseases. Further, the invention will be useful for treating multidrug resistance of tumor cells, (i.e. enhancing the activity and/or sensitivity of chemotherapeutic agents).

The compounds may be useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, nonA/nonB hepatitis, cirrhosis.

A. COMPOUNDS USEABLE IN ACCORDANCE WITH THIS INVENTION

As stated in the above-set-forth summary of the invention, the compounds of this invention are represented by Formula I below, Wherein, X, Y and Z are same or different and are independently selected from $CH_2$, O, S, $NR_1$, N=CH, CH=N and $R_2$—C=C—$R_3$, where $R_2$ and $R_3$ are H or may combine to form a saturated or unsaturated carbocyclic or heterocyclic ring, optionally substituted with one or more R groups;

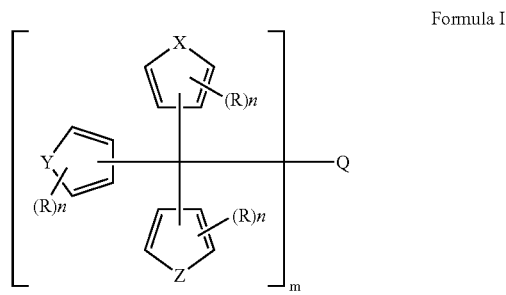

Formula I $R_1$ is selected from H, alkyl, alkenyl, alkynyl, cycloalkyl, aryl, acyl and aroyl, optionally substituted with hydroxy, amino, substituted amino, cyano, alkoxy, halogen, trihaloalkyl, nitro, thio, alkylthio, carboxy and alkoxycarbonyl groups;

R is selected from H, halogen, trihaloalkyl, hydroxy, acyloxy, alkoxy, alkenyloxy, thio, alkylthio, nitro, cyano, ureido, acyl, carboxy, alkoxycarbonyl, N—$(R_4)(R_5)$ and saturated or unsaturated, chiral or achiral, cyclic or acyclic, straight or branched hydrocarbyl group with from 1 to 20 carbon atoms, optionally substituted with hydroxy, halogen, trihaloalkyl, alkylthio, alkoxy, carboxy, alkoxycarbonyl, oxoalkyl, cyano and N—$(R_4)(R_5)$ group, $R_4$ and $R_5$ are selected from H, alkyl, alkenyl, alkynyl, cycloalkyl and acyl or $R_4$ and $R_5$ may combine to form a ring, wherein a carbon may be optionally substituted by a heteroatom selected from O, S or N—$R_6$, $R_6$ is H, alkyl, alkenyl, alkynyl, cycloalkyl, hydroxyalkyl or carboxyalkyl, n is 0–5; m is 1 or 2; with the proviso that when m is 1, Q is selected from OH, CN, carboxyalkyl, N—$(R_7)(R_8)$, where $R_7$ and $R_8$ are selected from H, lower alkyl (1–4C), cycloalkyl, aryl, acyl, amido, or $R_7$ and $R_8$ may combine to form a saturated or unsaturated heterocylic ring and optionally substituted with up to 3 additional heteroatoms selected from N, O, and S; or —NH-heterocycle, where the heterocycle is represented by thiazole, oxazole, isoxazole, pyridine, pyrimidine, and purine and where U and V are selected from H and O; and

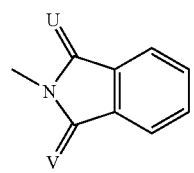

when m is 2, Q is a spacer of from 2–10 carbons either as a straight or branched, chiral or achiral, cyclic or acyclic hydrocarbon group, such as phenyl.

In the most preferred embodiment of this invention, X, Y, and Z are $R_2$—C=C—$R_3$, where $R_2$ and $R_3$ are H; R is selected from H and halogen, preferably, F and Cl; m is 1; and Q is —N—$(R_7)(R_8)$, where $R_7$ and $R_8$ are selected from H, acyl, amido, and $R_7$ and $R_8$ combine to form a saturated or unsaturated heterocyclic ring, optionally substituted with up to three heteroatoms selected from N, O, or S, for example, pyrrolidine, piperidine, pyrazole, oxazole, isoxazole, tetrazole, azepine, etc., which may be optionally substituted with a lower alkyl or amino group.

Some of the preferred compounds covered by Formula I include,
(2-chlorophenyl)diphenyl methanol (T3)
(2-thienyl)diphenyl methanol (T9)
N-[(2-chlorophenyl)diphenylmethyl]-urea (T33)
1-[(2-chlorophenyl)diphenylmethyl]-1H-pyrrole (T44)
N-[(2-chlorophenyl)diphenylmethyl]-N-(2-pyrimidyl) amine (T68)
(2-chlorophenyl)diphenylmethyl amine (T41)
N-(2-chlorophenyl)diphenylmethyl acetamide (T75)
2-(4-chlorophenyl)-2,2-diphenylacetonitrile (T26)
2-(2-chlorophenyl)-2,2-diphenylacetonitrile (T39)
2-[(2-chlorophenyl)(diphenyl)methyl]-1H-isoindole-1,3 (2H)-dione (T71)
1-[(2-chlorophenyl)diphenylmethyl]-1H-tetrazole (T84).

In another preferred embodiment having the general Formula I X, Y, and Z are each $R_2$—C=C—$R_3$ (where $R_2$ and $R_3$ are H;

R is selected from H and halogen, preferably, F and Cl); m is 2; and

Q is a spacer of from 2–10 carbons either as a straight or branched hydrocarbon chain, or containing a hydrocarbon ring such as phenyl. Some of the preferred compounds covered by this embodiment include:

N,N-1,2-ditritylamino ethane (T21)
1,4-ditritylaminomethyl benzene (T23)
N,N-1,3-[(2-chlorophenyl)diphenylmethyl]amino propane (T49).

Further in accordance with the invention, preferred compounds of this invention having the general Formula I above, are a group of triarylmethyl-1H-pyrazole compounds that have structural Formula I-A below:

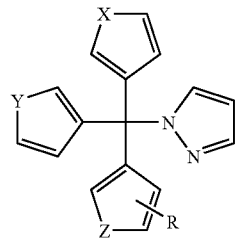

Formula I-A

Wherein:
X, Y, and Z are $R_2$—C=C—$R_3$, where $R_2$ and $R_3$ are H; R is selected from H and halogen, preferably, F and Cl; Preferred compounds covered by Formula I-A include,
1-[(2-chlorophenyl)diphenylmethyl]-1H-pyrazole (T34)
1-[(2-fluorophenyl)diphenylmethyl]-1H-pyrazole (T46)
1-[(4-chlorophenyl)diphenylmethyl]-1H-pyrazole (T13)
1-[(2-fluorophenyl)diphenylmethyl]-1H-pyrazole (T28)

B. SYNTHESIS OF THE COMPOUNDS

The compounds of this invention may be prepared as outlined in Scheme 1 and Example 1. The individual steps are described below in the examples. The synthetic procedures described here are exemplary and may be modified by those skilled in the art.

Scheme 1
Synthesis of triarylmethanes

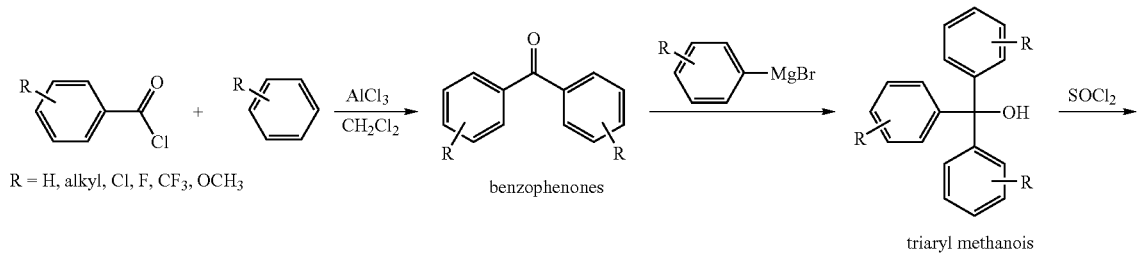

R = H, alkyl, Cl, F, CF₃, OCH₃ benzophenones triaryl methanois

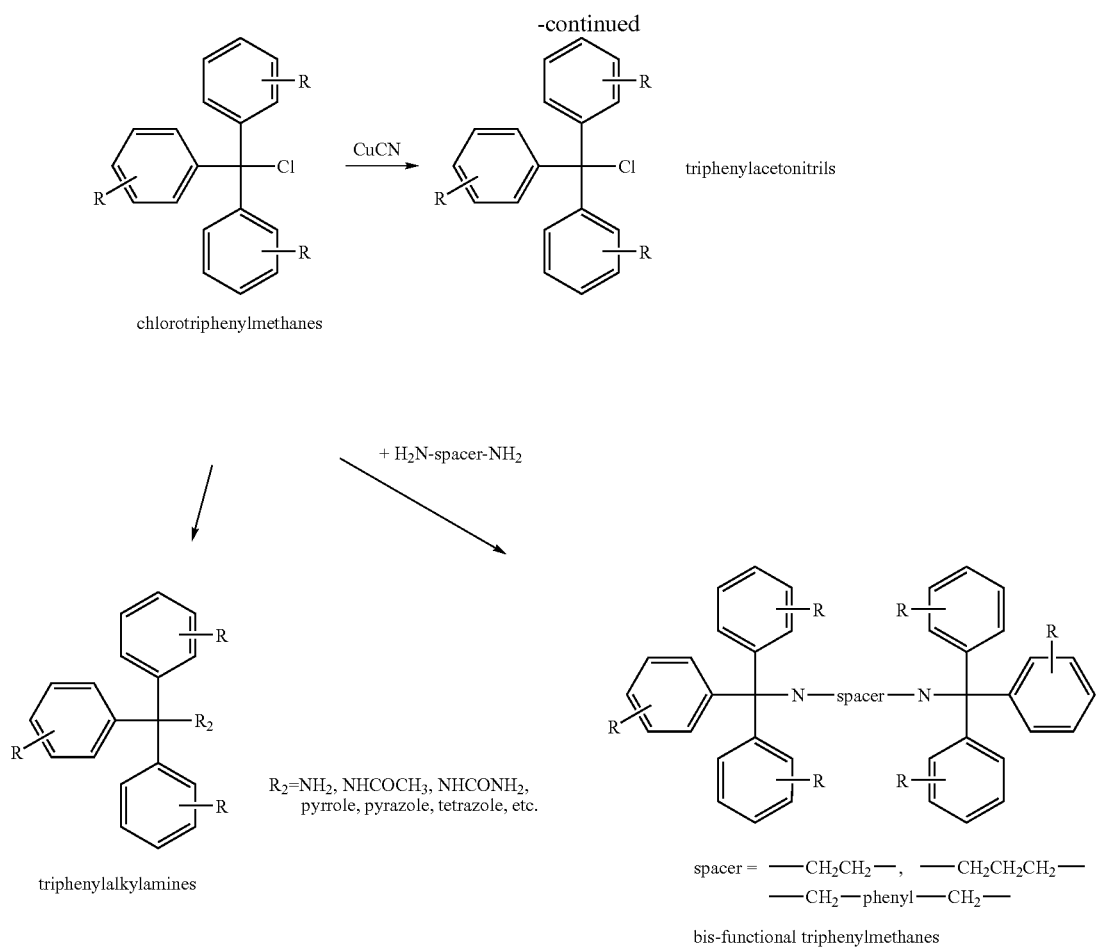

C. PREFERRED ROUTES OF ADMINISTRATION

The compounds described herein, or pharmaceutically acceptable salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts or hydrates thereof, may be administered singly or in combination with other therapeutic agents, e.g. analgesics, antibiotics, non-steroidal anti-inflammatory agents, steroids, and other immunosuppressive drugs like cyclosporin A, rapamycin, FK506 or Kv1.3 selective blockers. At least one of the preferred compounds, 1-[(2-chlorophenyl)diphenylmethyl]-1H-pyrazole designated as T34 in Appendix A, may be administered per se or in the form of a pharmaceutical composition wherein the active compound is in admixture with one or more physiologically acceptable carriers, excipients or diluents. Pharmaceutical compositions for use in accordance with the present invention may be formulated in conventional manner using one or more physiologically acceptable carriers comprising excipients and auxiliaries, which facilitate processing of the active compounds into preparations, which can be used pharmaceutically. Proper formulation is dependent on the route of administration chosen. For parenteral administration (bolus injection or continuous infusion), the agents of the invention may be formulated in water-soluble form in aqueous solutions, preferably in physiologically compatible buffers such as Hank's solution, Ringer's solution, or physiological saline buffer. Additionally, suspensions of the compounds may be prepared as oily injections with fatty oils, synthetic fatty acid esters, or liposomes. The compounds may also be formulated as a depot preparation. For oral administration, the compounds can be formulated readily by combining the active compound with pharmaceutically acceptable carriers well known in the art. Such carriers enable the compounds of the invention to be formulated as tablets, pills, dragees, capsules, liquids, gels, syrups, slurries, suspensions and the like, for oral ingestion for patients to be treated. Suitable excipients are, in particular, fillers such as sugars, including lactose, sucrose, mannitol, or sorbitol: cellulose preparations such as, for example maize starch, wheat starch, rice starch, potato starch, gelatin, gum tragacanth, methyl cellulose, hydroxypropyl-methylcellulose, sodium carboxymethylcellulose, and/or polyvinylpyrrolidone.

C. EXAMPLES

The following examples serve to illustrate various aspects of the invention and are not to be construed as limiting the invention to those embodiments so exemplified.

Example 1

Synthesis of Triarylmethanols (General Method A)

25 mmol of magnesium turnings and a catalytic amount of iodine to initiate the reaction were stirred in 50 ml of anhydrous diethyl ether. Then, a solution containing 25 mmol of the appropriate aryl bromide in anhydrous diethyl ether (50 ml) was slowly added allowing a gentle reflux. Once the addition was complete the mixture was heated at reflux until all the magnesium was consumed. Next, a solution of the required benzophenone (25 mmol) in anhydrous diethyl ether (50 ml) was slowly added. The resulting mixture was heated at reflux for 5–12 h, then cooled to 0° C. and poured into 100 ml of cold water. To dissolve the precipitating magnesium hydroxide the mixture was acidified with concentrated HCl. The organic phase was separated, and the aqueous phase was extracted with diethyl ether. The combined organic phases were washed with sodium bicarbonate solution (10%) and then dried over sodium sulfate. Evaporation of the solvent gave the respective triarylmethanol either as creamy solid or as an oil, which normally was recrystallized from petroleum ether (40–60° C.) several times.

Example 2

Preparation of (2-Chlorophenyl)diphenyl methanol (Compound T3)

Following the procedure outlined in Example 1, 1.3 g (52 mmol) of magnesium turnings, 10.0 g (52 mmol) of 1-bromo-2-chlorobenzene and 9.4 g (52 mmol) benzophenone gave 9.81 g (64%) of (2-Chlorophenyl) diphenyl methanol (Compound T3), mp: 91° C.

Example 3

Following the procedure outlined in Example 1, the following triarylmethanols (Table 1) were prepared.

TABLE 1

| Triarylmethanol Compound | Designation on Appendix A | Yield | Melting Point |
|---|---|---|---|
| (4-Chlorophenyl)diphenyl methanol | T1 | 56% | 82° C. |
| (3-Chlorophenyl)diphenyl methanol | T2 | 52% | 53° C. |
| Bis-(4-chlorophenyl)phenyl methanol | T4 | 56% | 86° C. |
| Bis-(3-chlorophenyl)phenyl methanol | T5 | 52% | oil |
| (2-Thienyl)diphenyl methanol | T9 | 64% | 129° C. |
| (4-Fluorophenyl)diphenyl methanol | T12 | 58% | 120.5° C. |
| (4-Fluorophenyl)(2-thienyl)phenyl methanol | T14 | 62% | 75° C. |
| Bis-(4-methoxyphenyl)phenyl methanol | T15 | 62% | sticky dark red paste |
| Tris-(4-methoxyphenyl) methanol | T16 | 48% | 75° C. |
| Di-(2-thienyl)phenyl methanol | T35 | 54% | 86° C. |
| (2-Fluorophenyl)diphenyl methanol | T36 | 69% | 116° C. |
| (2-Chlorophenyl)(2-thienyl)phenyl methanol | T43 | 58% | 90.5° C. |
| Diphenyl(2-trifluoromethylphenyl) methanol | T54 | 57% | 111° C. |
| Diphenyl(4-trifluoromethylphenyl) methanol | T55 | 68% | oil |
| Diphenyl(3-trifluoromethylphenyl) methanol | T56 | 62% | 52° C. |

Example 4

Synthesis of Triaryl Chlorides (General Method B)

To a stirred suspension of 20 mmol of the corresponding triarylmethanol in 100 ml of petroleum ether (40–60° C.) was added dropwise an excess of freshly distilled thionyl chloride. The reaction mixture was stirred at room temperature for 30 min and then heated under reflux for 1 h. Excess thionyl chloride was removed by concentrating to dryness in vacuo. The residue was suspended in 100 ml of petroleum ether and left in the refrigerator overnight. The resulting crystals were filtered off and thoroughly washed with petroleum ether. To avoid hydrolysis of these sensitive triaryl chlorides, they were immediately used for further reactions after being characterized by melting point and mass spectrometry.

Example 5

Synthesis of (2-Chlorophenyl)diphenyl chloromethane

Following the procedure outlined in Example 4, 5.00 g (17.1 mmol) of (2-chlorophenyl) diphenyl methanol, designated as T-3 on Appendix A, was treated with 2.5 ml thionyl chloride (34 mmol) according to general method B to give 4.39 g (82%) of (2-Chlorophenyl) diphenyl chloromethane, mp: 131° C.

Example 6

Synthesis of Triarylmethylamines (General Method C)

To a solution of the appropriate triaryl chloride (5 mmol) in anhydrous acetonitrile (100 ml) were added the desired amine or urea (5 mmol) and triethylamine (5 mmol) as proton acceptor. The resulting mixture was stirred and heated at reflux for 24 h. Evaporation of the solvent afforded a creamy residue, which was dissolved in 200 ml of methylene chloride. The mixture was washed two times with 50 ml of water, dried over $Na_2SO_4$, and concentrated in vacuo. The crude product was recrystallized from petroleum ether (40–60° C.)/methylene chloride.

Example 7

Preparation of 1-Tritylpyrrolidine (Compound T7)

2.00 g (7.2 mmol) of trityl chloride was treated with 0.51 g (7.2 mmol) pyrrolidine and 0.72 g (7.2 mmol) triethylamine according to General Method C in Example 6 to give 1.86 g (82%) of 1-tritylpyrrolidine (T7), mp: 126° C.

Example 8

Following the procedure in Example 6, the following compounds (Table 2) were prepared.

TABLE 2

| Triarylmethylamines from an amine or urea | Number | Yield | Melting Point |
|---|---|---|---|
| 1-Trityl-1H-pyrrole | T10 | 79% | 243° C. |
| N-trityl urea | T24 | 58% | 238° C. |
| N-[(4-Chlorophenyl)diphenylmethyl] urea | T29 | 62% | 228° C. |
| N-[(4-Fluorophenyl)diphenylmethyl] urea | T31 | 66% | 222° C. |
| N-[(2-Chlorophenyl)diphenylmethyl] urea | T33 | 68% | 243° C. |

TABLE 2-continued

| Triarylmethylamines from an amine or urea | Number | Yield | Melting Point |
|---|---|---|---|
| 1[(2-Chlorophenyl)diphenylmethyl]-1H-pyrrole | T44 | 67% | 184° C. |
| N-[(2-Fluorophenyl)diphenylmethyl] urea | T45 | 66% | 225° C. |

Example 9

Synthesis of Triarylmethylamines with a Heterocyclic amine (General Method D)

Especially with substituted pyrazoles and pyrimidines General Method C tended to give unsatisfactory yields and oily, dark byproducts, which where extremely difficult to remove even by column chromatography. Therefore excessive amine was used as a hydrogen acceptor instead of triethylamine. To a solution of the required triaryl chloride (5 mmol) in anhydrous acetonitrile (100 ml) was added an excess of the required amine (10–20 mmol). After stirring under reflux for 8 h the mixture was poured into cold water (400 ml) and kept at 4° C. for 2 h. The precipitate formed was collected by vacuum filtration, thoroughly washed with water to remove any of the remaining amine, and recrystallized from ethanol.

Example 10

Preparation of 1-[(2-Chlorophenyl)diphenylmethyl]-1H-pyrazole (Compound T34)

1.50 g (4.8 mmol) of 2-chlorotrityl chloride obtained under Example 5 was reacted with 1.00 g (15 mmol) of pyrazole according to general method D to give 1.26 g (76%) of 1-[(2-Chlorophenyl)diphenylmethyl]-1H-pyrazole, mp: 135° C.

Example 11

Following the procedure in Example 9, the following compounds (Table 3) were prepared.

TABLE 3

| Triarylmethylamines from Heterocyclic Amines | Designation on Appendix A | Yield | Melting Point |
|---|---|---|---|
| 1-Trityl-1H-pyrazole | T11 | 82% | 202° C. |
| 1[(4-Chlorophenyl)diphenylmethyl]-1H-pyrazole | T13 | 87% | 133° C. |
| 1-[Tris(4-methoxyphenyl)methyl]-1H-pyrazole | T19 | 82% | 158° C. |
| 1-[(4-Fluorophenyl)diphenylmethyl]-1H-pyrazole | T28 | 84% | 145° C. |
| 1-[Diphenyl(2-thienyl)methyl]-1H-imidazole | T37 | 78% | 176° C. |
| 1-[Diphenyl(2-thienyl)methyl]-1H-pyrazole | T38 | 83% | 157° C. |
| 1-[(2-Fluorophenyl)diphenylmethyl]-1H-pyrazole | T46 | 84% | 192° C. |
| N-(1,3-thiazol-2-yl)-N-tritylamine | T57 | 79% | 213° C. |
| 1-{Diphenyl[2-(trifluoromethyl)-phenyl]methyl}-1H-pyrazole | T58 | 46% | 114° C. |
| 1-{Diphenyl[2-(trifluoromethyl)-phenyl]methyl}-3-(trifluoromethyl)-1H-pyrazole | T59 | 62% | 107° C. |
| 1-{Diphenyl[4-(trifluoromethyl)-phenyl]methyl}-1H-pyrazole | T60 | 65% | 135° C. |
| N-Diphenyl[4-(trifluoromethyl)phenyl]-methyl-N-(1,3-thiazol-2-yl)amine | T61 | 58% | 166° C. |
| 1-[(2-Chlorophenyl)diphenylmethyl]-3,5-dimethyl-1H-pyrazole | T62 | 68% | 195° C. |
| 1-[(2-Chlorophenyl)diphenylmethyl]-3-methyl-1H-pyrazole | T63 | 78% | 118° C. |
| N-[(4-Chlorophenyl)diphenylmethyl]-N-(1,3-thiazol-2yl)amine | T64 | 62% | 156° C. |
| 1-[(2-Chlorophenyl)diphenylmethyl]-3-(trifluorormethyl)-1H-pyrazole | T65 | 64% | 139° C. |
| N-[(2-Chlorophenyl)diphenylmethyl]-N-(1,3-thiazol-2yl)amine | T66 | 72% | 152° C. |
| N-[(2-Chlorophenyl)diphenylmethyl]-N-(4-pyridyl)amine | T67 | 92% | 115° C. |
| N-[(2-Chlorophenyl)diphenylmethyl]-N-(2-pyrimidyl)amine | T68 | 64% | 162° C. |
| N-[(2-Chlorophenyl)diphenylmethyl]-N-(2-pyridyl)amine | T69 | 67% | 115° C. |
| N-[(4-Chlorophenyl)diphenylmethyl]-N-(4-pyridyl)amine | T70 | 81% | 214° C. |
| 2-[(2-Chlorophenyl)diphenylmethyl]-1H-isoindole-1,3(2H)-dione | T71 | 67% | 168° C. |
| N-Diphenyl[2-(trifluoromethyl)phenyl]-methyl-N-(1,3-thiazol-2yl)amine | T72 | 65% | 164° C. |
| N-Diphenyl[2-(trifluoromethyl)phenyl]-methyl-N-(2-pyrimidinyl)amine | T73 | 78% | 133° C. |
| N-[(2-Fluorophenyl)diphenylmethyl]-N-(1,3-thiazol-2yl)amine | T78 | 58% | 169° C. |
| N-[(2-Chlorophenyl)diphenylmethyl]-N-(4-methyl-1,3-thiazol-2yl)amine | T79 | 49% | 168° C. |
| N-{5-[(4-Nitrophenyl)sulfonyl]-1,3-thiazol-2yl}-N[(2-chlorophenyl)-(diphenyl)-methyl]amine | T81 | 73% | 135° C. |
| 1-[(2-Chlorophenyl)diphenylmethyl]-1H-1,2,3,4-tetrazole | T84 | 72% | 129° C. |
| 1-[(2-Chlorophenyl)diphenylmethyl]-1H-1,3-benzimidazole | T85 | 68% | 168° C. |

Example 12

Preparation of N,N-1,2-Ditritylamino ethane (Compound T21)

2.0 g (7.2 mmol) of trityl chloride, 0.21 g (3.6 mmol) of 1,2-diaminoethane and 0.72 g (7.2 mmol) of triethyl amine were dissolved in methylene chloride and heated under reflux for 8 hours as described under Example 6 (Ng 1995, *Tetrahedron* 51: 7883) to yield 1.03 g (53%) of N,N-1,2-ditritylamino ethane, mp: 172° C.

Example 13

The procedure in Example 12 was followed to obtain the following compounds (Table 4).

TABLE 4

| Bis-triarylmethyldiamines from Diamines | Number | Yield | Melting Point |
|---|---|---|---|
| N,N-1,3-Ditritylamino propane | T22 | 58% | 179° C. |
| 1,4-Ditritylaminomethyl benzene | T23 | 64% | 201° C. |
| N,N-1,2-[(2-Chlorophenyl)diphenylmethyl]-amino ethane | T48 | 62% | 228° C. |
| N,N-1,3-[(2-Chlorophenyl)diphenylmethyl]-amino propane | T49 | 58% | 198° C. |

Example 14

Preparation of (2-chlorophenyl)diphenylmethyl amine (Compound T41)

To a solution of 1.50 g (4.79 mmol) of (2-Chlorophenyl) diphenyl chloromethane, obtained under Example 5, in 100 ml of ethyl ether was added 100 ml of 25% ammonia solution and the resulting mixture was vigorously stirred at room temperature for 24 hours (Casadio 1973, *J. Pharm. Sci.* 62: 773). The organic layer was separated and the aqueous layer was extracted with ether. The combined organic phases were thoroughly washed with water, dried over anhydrous sodium sulfate and evaporated to dryness. The oily residue was crystallized from petroleum ether (40–60° C.) to give 1.10 g (78%) of the product, mp: 98° C.

Example 15

Following the procedure set forth in Example 14, the following three compounds were prepared (Table 5).

TABLE 5

| Triarylmethylamines from Ammonia | Number | Yield | Melting Point |
|---|---|---|---|
| (4-Fluorophenyl)diphenylmethyl amine | T42 | 81% | 62° C. |
| (2-Fluorophenyl)diphenylmethyl amine | T47 | 79% | 84° C. |
| (2-Trifluoromethylphenyl)-diphenylmethyl amine | T82 | 62% | 106° C. |

Example 16

Preparation of N-(2-chlorophenyl)diphenylmethyl acetamide (T75)

2.5 g (8.51 mmol) of (2-chlorophenyl) diphenylmethyl amine obtained under Example 14 was acetylated with 30 ml of freshly distilled acetic anhydride. The resulting mixture was stirred at 40° C. for 4 hours, poured into 200 ml of cold water and left in the refrigerator overnight. The precipitate was collected by vacuum filtration and recrystallized from ethanol to yield 1.17 g (41%) of the product, mp: 181° C.

Example 17

Following the procedure in Example 16 the following N-triarylmethyl acetamides were prepared from the corresponding amines obtained under Example 15 (Table 6).

TABLE 6

| N-Triarylmethylacetamides from corresponding Amines | Number | Yield | Melting Point |
|---|---|---|---|
| N-(2-Fluorophenyl)diphenylmethyl acetamide | T76 | 73% | 215° C. |
| N-(2-Trifluoromethylphenyl)diphenylmethyl acetamide | T83 | 83% | 185° C. |

Example 18

Preparation of 2-(4-Chlorophenyl)-2,2-diphenylacetonitrile (T26)

2-(4-Chlorophenyl) 2,2-diphenylacetonitrile was synthesized by carefully triturating 1.50 g (4.8 mmol) of 4-chlorotrityl chloride with 1.00 g (11 mmol) of copper cyanide and the resulting mixture was heated for 4 hours at 150° C. without a solvent. After cooling 50 ml of toluene was added, the mixture was filtered and the filtrate was concentrated in vacuo. The resulting residue was recrystallized from petroleum ether (40–60° C.) to give 0.66 g (45%) of the triarylmethyl acetonitrile derivative.

Example 19

The following triarylmethyl acetonitriles were prepared by the procedure outlined in Example 18 (Table 7)

TABLE 7

| Triarylmethylacetonitriles from corresponding Chlorides | Number | Yield | Melting Point |
|---|---|---|---|
| 2-(4-Fluorophenyl)2,2-diphenylacetonitrile | T27 | 52% | 76° C. |
| 2-(2-Chlorophenyl)2,2-diphenylacetonitrile | T39 | 52% | 143° C. |
| 2-(2-Fluorophenyl)2,2-diphenylacetonitrile | T40 | 63% | 144° C. |

Compounds T39 and T40 have been disclosed in Brugnara, PCT Application WO 97/34589. Compounds T50 (4-pyridyl,diphenyl methanol), T51 (2,2,2-Triphenyl propionic acid), T52 [(S)-(−)-α,α-diphenyl-2-pyrrolidine methanol] and T53 [(R)-(+)-α,α-diphenyl-2-pyrrolidine methanol] used in the biological testing are commercially available from Aldrich Chemical. Co., Milwaukee, Wis. 53201, USA.

The following example provides an exemplary, but not limiting, formulation, for administering the compounds of the invention to mammals. Any of the compounds described herein, or pharmaceutically acceptable salts or hydrates thereof, may be formulated as illustrated in the following example.

Example 20

Gelatin Capsules

Acid-resistant coated hard gelatin capsules are prepared using the following ingredients:

| | |
|---|---|
| Compound T34 | 100 mg/capsule |
| Starch dried | 200 mg/capsule |
| Magnesium stearate | 10 mg/capsule |

The above ingredients are mixed and filled into acid-resistant coated hard gelatin capsules in 310 mg quantities.

Example 21

In Vitro Activity

The assays are generally applicable for demonstrating the in vitro activity of compounds of General Formula (I).

A) Block of IKCa1

This example demonstrates the ability of the exemplary compounds, to inhibit the cloned human IKCa1 channel. The cloning of human IKCa1 has been previously reported (Fanger 1999, *J. Biol. Chem.* 274: 5746). COS-7 cells, maintained in Dulbecco's modified Eagle's medium (DMEM) containing 10% heat-inactivated fetal calf serum, 4 mM L-glutamine and 1 mM $Na^+$ pyruvate, were transiently transfected with hIKCa1.

Electrophysiological experiments were carried out in the whole-cell configuration of the patch-clamp technique using an EPC-9 amplifier (HEKA Elektronik, Lambrecht Germany) interfaced to a computer running acquisition and analysis software (Pulse and Pulsfit; HEKA Elektronik). Pipettes were pulled from soft glass capillaries, coated with Sylgard (Dow-Corning, Midland, Mich.), and fire polished to resistances of 2.0–4.5 MΩ measured in the bath. COS-7 cells were trypsinized and plated on glass coverslips 3 h before measurement. For measurements of $IK_{Ca}$ currents an internal pipette solution containing 145 mM $K^+$ aspartate, 2 mM $MgCl_2$, 10 mM HEPES, 10 mM $K_2EGTA$ and 8.5 mM $CaCl_2$ (rendering 1 µM of free $Ca^{++}$), adjusted to pH 7.2 with NaOH, with an osmolarity of 290–310 mosM was used. To prevent activation of the native chloride channels in COS-7 cells an aspartate Ringer solution was used as an external solution (160 mM $Na^+$ aspartate, 4.5 mM KCl, 2 mM $CaCl_2$, 1 mM $MgCl_2$, 5 mM HEPES, adjusted to pH 7.4 with NaOH, with an osmolarity of 290–310 mosM). 200 ms voltage ramps from −120 mV to 40 mV every 10 s were used. The holding potential in all experiments was −80 mV. Series resistance compensation was not employed. The reduction of slope conductance at −80 mV was used to determine the $K_d$-value by fitting the values to the Hill equation with a Hill coefficient of unity.

The results of this assay are provided in TABLE 8, below.

TABLE 8

$K_d$ values for block of IKCa1 stably transfected into COS-7 cells

| Compound Designation in Appendix A | $K_d$ [nM] |
|---|---|
| T1 | 550 |
| T2 | 530 |
| T3 | 520 (±30) |
| T4 | No effect at 1 µM |
| T5 | No effect at 1 µM |
| T7 | 30000 |
| T8 | No effect at 10 µM |
| T9 | 1500 |
| T10 | 28000 |
| T11 | 2500 (±400) |
| T12 | 700 |
| T13 | 90 (±10) |
| T14 | 800 |
| T15 | 10000 |
| T16 | 10000 |
| T17 | 35000 |
| T18 | 40000 |
| T19 | No effect at 1 µM |
| T20 | No effect at 1 µM |
| T23 | No effect at 1 µM |
| T24 | 8000 |
| T26 | 750 |
| T27 | 800 |
| T28 | 200 |
| T29 | 15000 |
| T30 | 10000 |
| T31 | 8000 |
| T34 | 20 (±3) |
| T35 | 9000 |
| T36 | 700 |
| T37 | 1000 |
| T38 | 1100 (±100) |
| T39 | 60 |
| T40 | 60 |
| T41 | 5000 |
| T42 | 5000 |
| T43 | 750 |
| T45 | 1000 |
| T46 | 40 (±5) |
| T47 | 2000 |
| T48 | 30000 |
| T49 | 32000 |
| T54 | 700 |
| T55 | 820 |

TABLE 8-continued $K_d$ values for block of IKCa1 stably transfected into COS-7 cells

| Compound Designation in Appendix A | $K_d$ [nM] |
|---|---|
| T56 | 650 |
| T57 | n.d. |
| T58 | 5000 |
| T59 | 25000 (±3) |
| T60 | 1500 (±0.3) |
| T61 | 35000 |
| T62 | 12000 |
| T63 | 1100 (±0.3) |
| T64 | 20000 |
| T65 | 2000 (±0.5) |
| T66 | 15000 |
| T67 | 30000 |
| T68 | 900 |
| T69 | 28000 |
| T70 | 11000 |
| T71 | No effect at 10 µM |
| T72 | 25000 |
| T73 | 15000 |
| T74 | 600 |
| T75 | 1200 |
| T76 | 1200 |
| T77 | 800 |
| T78 | 12000 |
| T79 | 8000 |
| T81 | 15000 |
| T82 | 2500 |
| T83 | 1500 |
| T84 | 45 (±7) |
| T85 | No effect at 1 µM |
| T86 | 1500 (±500) |

B) Selectivity of Clotrimazole and 1-[(2-Chlorophenyl) diphenylmethyl]-1H-pyrazole (T34) for IKCa1 Over Other Ion Channels 1-[(2-Chlorophenyl)diphenylmethyl]-1H-pyrazole (T34) was judged to be the most potent compound of the exemplary compounds covered by General Formula (I) and was further investigated for its selectivity over a whole range of other ion channels. Clotrimazole, the imidazole currently under clinical investigation for the treatment of sickle cell disease and diarrhea was used as a control. 1-[(2-chlorophenyl)diphenylmethyl]-1H-pyrazole (T34) was also investigated for its ability to block native IKCa1 currents in activated human T-lymphocytes and in the human colonic epithelial cell line T84.

L929 cells stably expressing mKv1.1, rKv1.2, mKv1.3, and mKv3.1 and MEL cells stably expressing hKv1.5 have been previously described (Grissmer 1994, *Mol. Pharmacol.* 45: 1227). hKv1.4 and rKv4.2 were stably expressed in LTK (HK1–7). Channel expression was induced 8–12 h before the electrophysiological experiments by 4 µM dexamethasone (Sigma). HEK-293 cells stably expressing the skeletal muscle sodium channel hSkM1 (SCN4A) were generated in the laboratory of Dr. F. Lehmann-Horn. HEK-293 cells stably expressing hSloα were obtained from Dr. Andrew Tinker (Center for Clinical Pharmacology, University College London). L929, MEL, LTK and HEK cells were maintained in DMEM containing 10% heat-inactivated fetal calf serum (Summit Biotechnology, Fort Collins, Colo.) and 250 µg/ml G418 (Life Technologies, Inc.). Rat basophilic leukemia (RBL) cells were maintained in Eagle's minimum essential medium with 2 mM L-glutamine and 10% fetal calf serum. CHO cell were maintained in F12K media (ATCC). Human leukemic Jurkat E6–1 cells were cultured in RPMI 1640 supplemented with 10% fetal calf serum and 1 mM L-glutamine. T84 cells were maintained in a 1:1 mixture of Ham's F12 medium and DMEM with 2.5 mM L-glutamine and 10% fetal calf serum.

Human peripheral blood mononuclear cells (PBMC) were isolated from heparinized blood samples of healthy volunteers using a lymphocyte separation medium (Accuspin System-Histopaque-1077, Sigma Diagnostics) and maintained in RPMI 1640 supplemented with 10% fetal calf serum, 1 mM L-glutamine, 1 mM Na pyruvate, 1% non essential amino acids. Purified T-lymphocytes were prepared by passage through a nylon wool column. Activated T cell blasts were prepared by treating the resting cells with 1 µg/ml phytohemagglutinin (PHA-P, DIFCO, Detroit, Mich.).

Recordings from the Jurkat $SK_{Ca}$ channel were made in $K^+$ aspartate Ringer ($Na^+$ was replaced by $K^+$) with the same internal pipette solution. Recordings form the RBL inward rectifier (rKir2.1) were made in aspartate Ringer with a $K^+$ aspartate based pipette solution containing 50 nM of free $Ca^{++}$. No ATP was added to the pipette solution, because within 15 min of recording we witnessed no significant channel rundown. For both $SK_{Ca}$ and inward rectifier currents the reduction of slope conductance at −110 mV from 200 ms voltage ramps from −120 mV to 40 mV every 10 s was taken as a measure of channel block. $BK_{Ca}$ currents were elicited by 200 ms voltage ramps from −80 to 80 mV every 30 s. In aspartate Ringer with 1 µM of free $Ca^{++}$ in the pipette solution currents turned on at −20 mV and the reduction of slope conductance at 35 mV was used to evaluate channel block. For measurements of Kv currents cells were bathed in normal Ringer solution (160 mM NaCl, 4.5 mM KCl, 2 mM $CaCl_2$, 1 mM $MgCl_2$, 10 mM HEPES) and an internal pipette solution containing 134 mM KF, 2 mM $MgCl_2$, 10 mM HEPES, 10 mM EGTA, adjusted to pH 7.2 with NaOH, with an osmolarity of 290–310 mosM, was used. For recordings from Kv1.1, Kv1.3, Kv1.4, Kv1.5, Kv3.1 and Kv4.2 the voltage was stepped to 40 mV from the holding potential for 200 ms every 30 s. $K_d$-values were determined by fitting the Hill equation to the reduction of peak current. For Kv1.2, because of its "use-dependent" activation, a different pulse protocol was used: 300 ms every 10 sec, and the reduction of the mean of the current between 80–100% of the pulse duration was fitted to the Hill equation. For sodium channel recordings we employed voltage steps to −15 mV every 10 sec. Series resistance compensation (60–80%) was used if currents exceeded 1 nA. Capacitative and leak currents were subtracted using the P/8 procedure. Whole-cell recordings of monovalent currents through Jurkat CRAC channels with $Na^+$ as the charge carrier were made as previously described (Kerschbaum 1999, Science 283: 836). For measurements of swelling-activated mini chloride currents (Ross 1994, Biophys. J. 66: 169) 3 days activated human T-lymphocytes were bathed in normal Ringer solution (290 mosM) and a hypertonic internal pipette solution containing 160 mM Cs glutamate, 2 mM $MgCl_2$, 10 mM HEPES, 0.1 mM $CaCl_2$, 1.1 mM EGTA, 4 mM $Na_2ATP$ and 100 mM sucrose, adjusted to pH 7.2 with CsOH, with an osmolarity of 420 mosM, was used. Chloride currents were elicited by the same voltage ramps as $IK_{Ca}$ currents and blocking potency of the compounds on the slope conduction at −40 mV was evaluated between 300 and 900 s after break-in. A simple syringe-driven perfusion system was used to exchange the bath solution in the recording chamber.

Figure 1B:
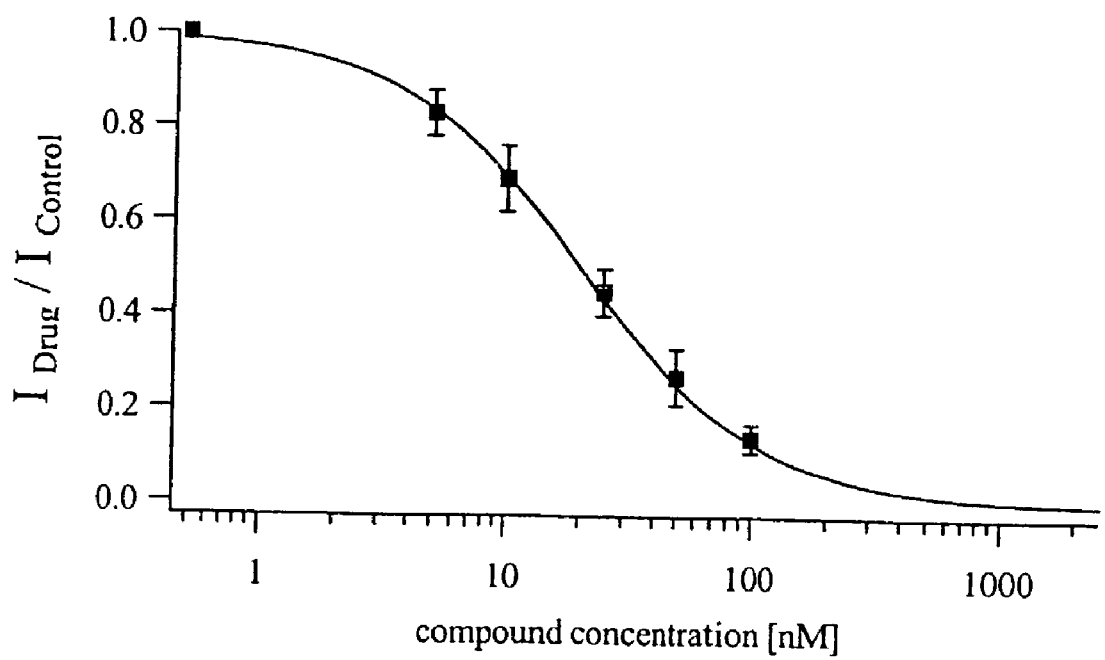
FIG. 1b shows the Hill plot (nH=1.8) of the reduction of slope conductance at −80 mV of IKCa1 currents in COS-7 cells (n=15).
Figure 1C:
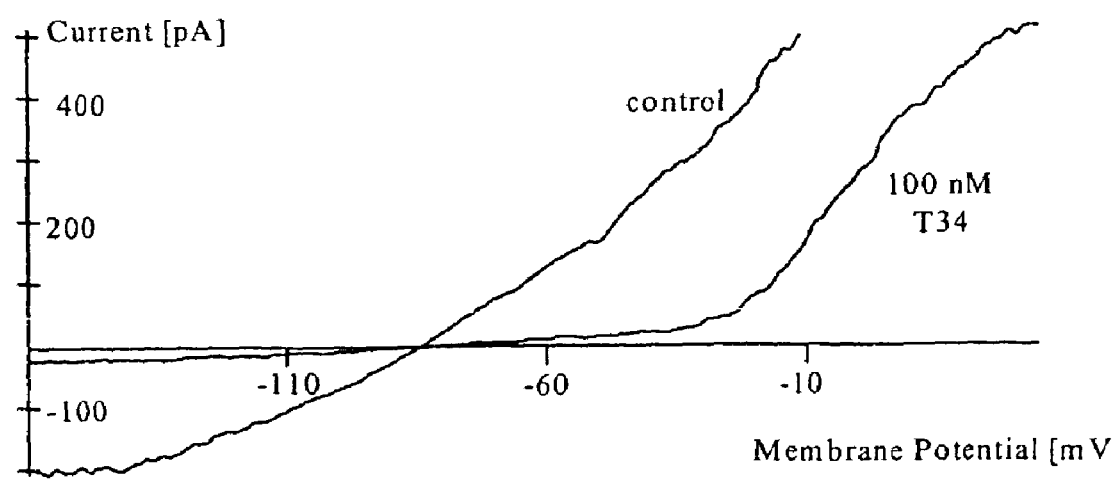
FIG. 1c is a graph showing the effect of 100 nM of T34 on native $IK_{Ca}$ currents in a human T-lymphocyte after 4 days of activation with 1 μg/ml PHA. Currents were elicited by 200 ms voltage ramps from −160 to 40 mV every 30 s with 1 μM of free $Ca^{++}$ in the pipette solution.

The results of this assay are provided in TABLE 9, below. The effect of 100 nM of 1-[(2-chlorophenyl)diphenylmethyl]-1H-pyrazole (T-34 in Appendix A) on cloned and native IKCa1 currents is shown in FIG. 1. As shown in TABLE 9 and FIGS. 1a–1c, 1-[(2-chlorophenyl)diphenylmethyl]-1H-pyrazole (T34) is a highly potent and selective blocker of both cloned and native IKCa1 currents. Contrary to Clotrimazole, 1-[(2-chlorophenyl)diphenylmethyl]-1H-pyrazole (T34) does not inhibit the activity of CYP3A4, the major xenobiotic metabolizing enzyme of human liver (see TABLE 9).

TABLE 9

| | Channel | Clotrimazole [nM] | T34 [nM] |
|---|---|---|---|
| $IK_{Ca}$ | hIKCa1 | 70 ± 10 (n = 9) | 20 ± 3 (n = 15) |
| | lymphocyte IK | 100 | 25 ± 5 (n = 9) |
| | T84 IK | 90 ± 15 (n = 9) | 22 ± 10 (n = 9) |
| K | mKv1.1 | 10000 ± 850 (n = 9) | 9500 ± 1000 (n = 9) |
| | rKv1.2 | 5000 ± 730 (n = 9) | 4500 ± 520 (n = 9) |
| | mKv1.3 | 6000 ± 440 (n = 9) | 5000 ± 350 (n = 9) |
| | hKv1.4 | 6000 ± 520 (n = 9) | 7500 ± 410 (n = 9) |
| | hKv1.5 | 8000 ± 890 (n = 9) | 7000 ± 620 (n = 9) |
| | mKv3.1 | 33000 ± 4000 (n= 9) | 30000 ± 5000 (n = 9) |
| | rKv4.2 | 8000 ± 950 (n = 9) | 6000 ± 870 (n = 9) |
| | Jurkat-SK | 22000 ± 1200 (n = 6) | 23000 ± 2000 (n = 6) |
| | BK (hSloα) | 24000 ± 2000 (n = 9) | 25000 ± 1800 (n = 9) |
| | rKir2.1 | no effect at 10 µM (n = 3) | no effect at 10 µM (n = 3) |
| Na | HSKM1 | 7000 ± 550 (n = 9) | 8000 ± 600 (n = 9) |
| Ca | Jurkat-CRAC | no effect at 10 µM (n = 2) | no effect at 10 µM (n = 2) |
| Cl | Lymphocyte swelling-activated | not done | 10000 ± 3000 (n = 4) |
| | COS-7 | no effect at 10 µM (n = 5) | no effect at 10 µM (n = 5) |
| $EC_{50}$ for inhibition of CYP3A4 | | 30 (99% inhibition at 100 | No inhibitory effect at 10 µM (n = 2) |

C) Inhibition of Cytochrome P450 3A4 Catalytic Activities by a Single Concentration of 10 Test Substances The test substances shown in Table 8 were evaluated for their inhibitory effect on the catalytic activity of human cytochrome P450 enzyme. Cytochrome P450 3A4 (CYP3A4) is involved in many drug-drug interactions and in many other pathways in the body including the catabolism of steroids and xenobiotics. Inhibition of this enzyme was measured in 96 well plates with 7-benzyloxy-4-trifluoromethylcoumarin (BFC) as the substrate and cDNA-derived enzymes in microsomes prepared from baculovirus-infected insect cells.

The inhibition study consisted of the determination of inhibition by the test substance on CYP3A4 catalytic activity. A single concentration of each model substrate (approximately the apparent $K_m$) and one test substance concentration (10 µM), were tested in duplicate. The compounds were prepared as 10 mM stock solutions in acetonitrile. Metabolism of the model substrate was assayed by the production of 7-hydroxy-4-trifluoromethylcoumarin metabolite. The metabolite was detected by fluorescence.

Table 10 below provides a list of the name of enzymes examined, the catalog number of the microsomes used as a source of the enzyme, the concentration of the model substrate used, the amount of enzyme used, the final buffer concentration, and the positive control compound.

TABLE 10

| Enzyme | CYP3A4 |
|---|---|
| Catalog Number | P202 |
| Substrate | BFC |
| Substrate Concentration | 50 µM |

TABLE 10-continued

| | |
|---|---|
| Pmole Enzyme per Well | 1–2 |
| Potassium Phosphate Buffer Concentration | 200 mM |
| Positive Control (Concentration) | ketoconazole (5 µM) |

Assays were conducted in 96 well microtiter plates. The BFC substrate was initially prepared in acetonitrile. The final concentration of the substrate was 50 µM, which is below the apparent $K_m$. Six wells were used for one test. Wells 1 and 2 contained a 10 µM concentration of the test substance (except clotrimazole, which had 0.1 µM), and wells 3 and 4 contained no test substance and wells 5 and 6 were blanks for background fluorescence (stop solution added before the enzyme). For the positive controls, 12 wells in a row were used for one test. The positive control inhibitor/enzyme combination was examined in duplicate rows. Wells 1 to 8 contained serial 1:3 dilutions of the inhibitors. The highest inhibitor concentration were as described in the table above. Wells 9 and 10 contained no inhibitor and wells 11 and 12 were blanks for background fluorescence (stop solution added before the enzyme).

After buffer, cofactors and inhibitor addition, the plates were pre-warmed to 37° C. Incubations were initiated by the addition of pre-warmed enzyme and substrate. The final cofactor concentrations were 1.3 mM NADP, 3.3 mM glucose-6-phosphate and 0.4 U/ml glucose-6-phosphate dehydrogenase. The final incubation volume was 0.2 ml. Incubations were carried out for 30 minutes [CYP3A4 (BFC)] and stopped by the addition of 0.075 ml of 80% acetonitrile-20% 0.5M Tris. Fluorescence per well was measured using a BMG FLUOstar fluorescence plate reader. The BFC metabolite 7-hydroxy-4-trifluoromethyl-coumarin was measured using an excitation wavelength of 410 nm and emission wavelength of 538 nm.

All results listed in Table 11 are consistent with a properly functioning model with 0.1 µM of clotrimazole producing 99% of inhibition. The ambivalent effects (e.g. inhibition or activation) on CYP3A4 catalytic activity by some compounds is commonly observed with CYP3A4. One explanation for this is that the enzyme is capable of accommodating 2 or more compounds simultaneously, one of which may activate, or inhibit metabolism of the other (Thummel 1998, Ann. Rev. Pharmacol. Toxicol. 38: 389). Although activation of CYP3A4 enzymatic activity is commonly observed in vitro, to our knowledge, this has not been demonstrated in vivo in humans. It appears that the compounds designated as T3, T34, T58 and T75 on Appendix A have the potential for activation metabolism of compounds that are substrates for CYP3A4.

TABLE 11

Percent of inhibition of catalytic activity of CY3A4

| Test compound | concentration | % inhibition |
|---|---|---|
| T3 | 10 µM | −30.5 |
| T34 | 10 µM | −77.5 |
| T39 | 10 µM | 10 |
| T40 | 10 µM | 9 |
| T58 | 10 µM | −26 |
| T66 | 10 µM | 86.5 |
| T67 | 10 µM | 74 |
| T74 | 10 µM | 4 |
| T75 | 10 µM | −54 |
| clotrimazole | 0.1 µM | 99 |

D) In Vitro Toxicity

The in vitro toxicity was performed as follows. Jurkat E6-1, MEL, $C_2F_3$, NGP, NLF cells and human T-lymphocytes were seeded at $5 \times 10^5$ cells/ml, and L929, COS-7, CHO and RBL cells were seeded at $10^5$ cells/ml in twelve-well plates. Drug (2 or 5 µM) was added in a final DMSO concentration of 0.1%. After 48 h of incubation at 37° C. with 5% $CO_2$, cells were harvested by sucking them off the plates (suspension cells) or by trypsinization (adherent cell lines). Cells were centrifuged, resuspended in 0.5 ml PBS containing 1 µg/ml propidium iodide (PI), and red fluorescence measured on a FACScan flow cytometer after 20 min, $10^4$ cells of every sample being analyzed. The percentage of dead cells was determined by their PI uptake. Two controls for every cell line (one in medium and one with 0.1% DMSO) were also analyzed.

The results of this in vitro toxicity assay are shown in TABLE 12. 1-[(2-chlorophenyl)diphenylmethyl]-1H-pyrazole (T34 in Appendix A), at a concentration 100–250 times the $K_d$ for IKCa1 channel block, did not reduce cell viability in any of the ten cell lines examined.

TABLE 12

| Cells* | Control | control 0.1% DMSO | 2 µM T34 | 5 µM T34 |
|---|---|---|---|---|
| T-lymphocytes | 6.1 | 7.1 | 6.2 | 7.0 |
| Jurkat E6-1 | 3.2 | 2.3 | 2.5 | 3.2 |
| MEL | 5.1 | 4.8 | 6.2 | 5.8 |
| L929 | 9.6 | 7.8 | 4.6 | 7.5 |
| COS-7 | 4.5 | 4.0 | 3.6 | 4.5 |
| CHO | 4.6 | 5.6 | 5.6 | 4.7 |
| RBL-2H3 | 5.5 | 7.6 | 7.9 | 8.8 |
| $C_2F_3$ | 17.4 | 14.3 | 15.8 | 12.8 |
| NLF | 12.8 | 9.1 | 10.8 | 10.8 |
| NGP | 8.0 | 4.2 | 10.9 | 5.9 |

*MEL, murine erythroleukemia cells; L929, murine fibrosarcoma cell; COS-7, SV40 transformed African green monkey kidney; CHO, Chinese hamster ovary cells; RBL-2H3, rat basophilic leukemia cells; Jurkat E6-1, human leukemic T-cell line; $C_2F_3$ human myoblasts; NGP and NLF human neuroblastoma cell lines.

E) Acute In Vivo Toxicity

An ISO acute systemic toxicity study was performed in CF-1 BR mice (17–19 g) according to the guidelines of the United States Pharmacopeia XXII. Five mice were injected intravenously with a single 0.9–1.0 ml (50 ml/kg) dose of 0.5 mg/kg 1-[(2-chlorophenyl)diphenylmethyl]-1H-pyrazole (T34) (29 µM in mammalian Ringer solution with 1% ethanol and 2.5% bovine serum albumin). Mice were observed for adverse effects immediately after dosing, at 4 h after injection and daily for 7 days. Five control mice were injected with an equal volume of the vehicle. The mice were weighed at the beginning of the study and at its termination.

The results clearly showed that there was no mortality and all animals appeared clinically normal during the 7-day study. The body weight data of the test compound treated group (wt on day 1:17.8 g; wt on day 7: 27.0 g) were similar to controls (day 1: 17.4 g; day 7: 23.4 g) during the study. These data, taken together with the data from the cell viability assay, suggest that 1-[(2-chlorophenyl)diphenylmethyl]-1H-pyrazole (T34) was not toxic at ~100–1000 times the pharmacological dose thus exhibiting a very good therapeutic index.

F) Hydrolytic Stability of 1-[(2-Chlorophenyl)diphenylmethyl]-1H-pyrazole (T34) vs. Clotrimazole Applicants investigated the stability of 1-[(2-chlorophenyl)diphenylmethyl]-1H-pyrazole (T34 in Appendix A) against hydrolysis at pH 7.4 and at pH 5.0. The resulting concentrations of compound T34 and its expected degradation product (2-chlorophenyl)diphenyl methanol (T3) in analogy to clotrimazole were determined by HPLC.

To access oral bioavailability the stability of 1-[(2-chlorophenyl)diphenyl methyl]-1H-pyrazole (T34 in Appendix A) under acidic conditions was determined at pH 1 in artificial stomach fluid (DAB9).

A Waters 590 liquid chromatograph with a Waters 746 integrator and a Waters 486 UVN is detector, and a 25 cm Lichrospher RP18 column (5-μM particle size) was used. The mobile phase consisted of $K_2HPO_4$ 25 mM, $KH_2PO_4$ 30 mM, methanol at 262:13:725. The chromatographic separation was performed at 20° C. with a flow rate of 1.0 ml/min, the absorbance of the elluent was monitored at 210 nm.

Hydrolysis profiles (10 μM compound with 20% acetonitrile) were carried out in Soerensen phosphate buffer (pH 7.4 and pH 5.0) in a total volume of 10 ml. 100 μl samples were collected 0, 1, 2, 3, 4, 5, 24, 48 and 72 hours after incubation, with shaking, in a waterbath at 37° C. and manually injected into the HPLC over Rheodyne 7125 system. For profiles at pH 1.0 artificial stomach fluid (DAB 9), containing 2 g NaCl, 3,2 g pepsin and 80 ml 1 M HCL in 1.0 L of water was used. After 0, 1 and 2 hours 400 μl of sample were collected and extracted three times with 500 μl of ethyl ether by vortexing. The combined extracts were than evaporated to dryness by passing nitrogen through the solution. The residue was than dissolved in 400 μl of mobile phase of which 100 μM were injected in the HPLC. The recovery rate from this extraction procedure was 80%.

This chromatographic system gave retention times of 16.1 min for T3, 20.6 min for clotrimazole and 23.4 min for T34. Whereas clotrimazole slowly hydrolyzed at pH 5.0 (22% T3 after 48 h, 35% T3 after 72 h), T34 was completely stable against hydrolysis at pH 7.4 and pH 5.0 over 72 h (see FIG. 2).

Figure 2:
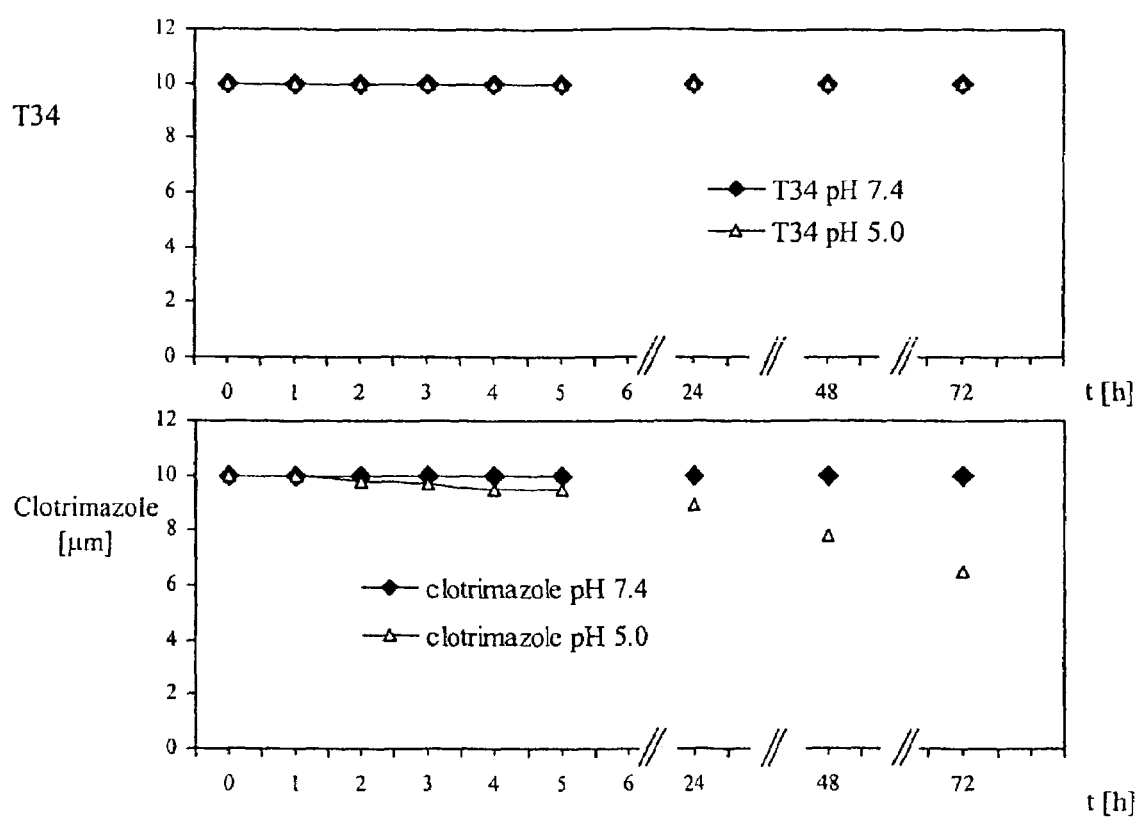
FIG. 2 shows the hydrolysis of compound T34 and clotrimazole at pH 7.4 and pH 5.0.
Figure 3:
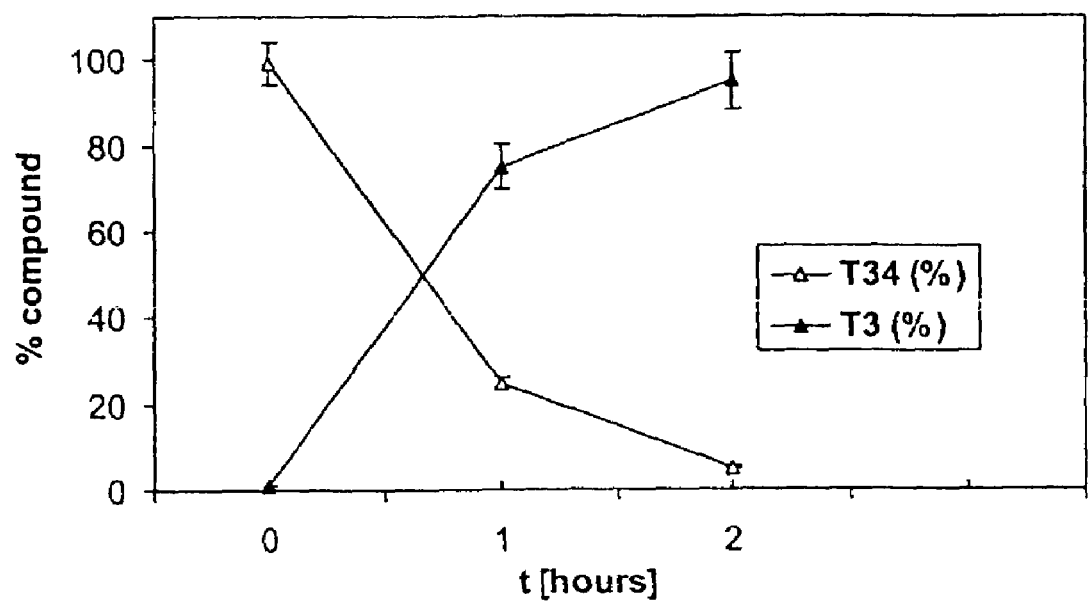
FIG. 3 shows the hydrolysis of compound T34 to T3 at pH1.

As shown in FIG. 2, the results clearly show that compound T34 was completely stable against hydrolysis at pH 10, pH 7.4 and pH 5.0 over 72 h (pH 10.0 is not shown). Specifically, FIG. 2 shows the hydrolysis of compound T34 and clotrimazole at pH 7.4 and pH 5.0 (for clotrimazole at pH 5.0 the corresponding amount of T3 can be detected at the corresponding retention time (mean of 3 determinations). At pH 1.0 T34 rapidly breaks down to T3 with a half-life of ~45 min (FIG. 3).

These results demonstrate that T34 can be used in T-lymphocyte proliferation and cytokine secretion assays. However, for oral administration T34 should be used in an acid-resistant coated formulation.

The compounds of this invention, or pharmaceutically acceptable salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections. The compounds described herein, or pharmaceutically acceptable salts or hydrates thereof, may be administered singly or in combination with other therapeutic agents, e.g. analgesics, antibiotics and other immunosuppressive drugs like cyclosporin A or Kv1.3 selective blockers. The active compound (T34) may be administered per se or in the form of a pharmaceutical composition wherein the active compound is in admixture with one or more physiologically acceptable carriers, excipients or diluents. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent on the route of administration chosen. For parenteral administration (bolus injection or continuous infusion), the agents of the invention may be formulated in water soluble form in aqueous solutions, preferably in physiologically compatible buffers such as Hank's solution, Ringer's solution, or physiological saline buffer. Additionally, suspensions of the compounds may be prepared as oily injections with fatty oils, synthetic fatty acid esters, or liposomes. The compounds may also be formulated as a depot preparation. For oral administration, the compounds can be formulated readily by combining the active compound with pharmaceutically acceptable carriers well known in the art. Such carriers enable the compounds of the invention to be formulated as tablets, pills, dragees, capsules, liquids, gels, syrups, slurries, suspensions an the like, for oral ingestion for patients to be treated. Suitable excipients are, in particular, fillers such as sugars, including lactose, sucrose, mannitol, or sorbitol: cellulose preparations such as, for example maize starch, wheat starch, rice starch, potato starch, gelatin, gum tragacanth, methyl cellulose, hydroxypropyl-methylcellulose, sodium carboxymethylcellulose, and/or polyvinylpyrrolidone.

APPENDIX A

Exemplary Compounds

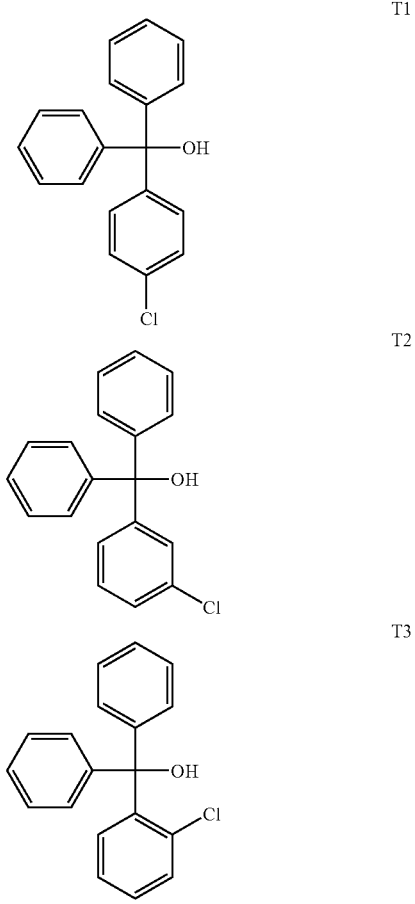

-continued
T4
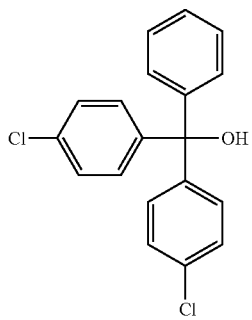
T5
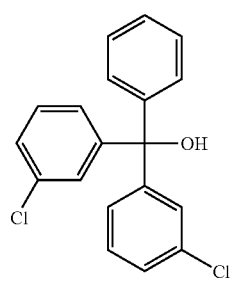
T7
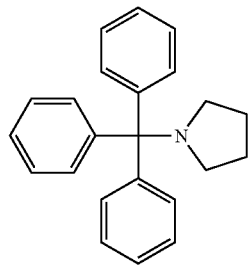
T8
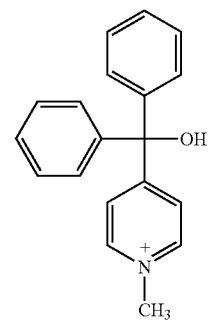
T9
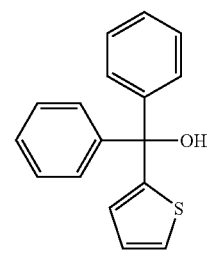
-continued
T10
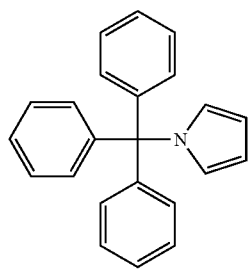
T11
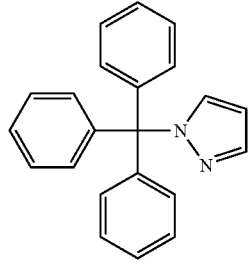
T12
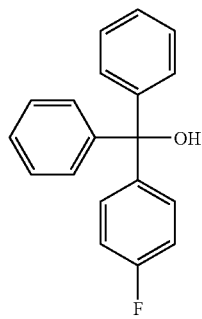
T13
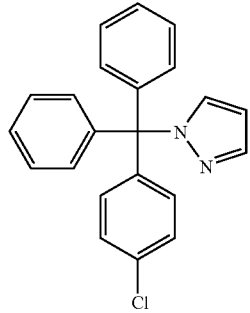
T14
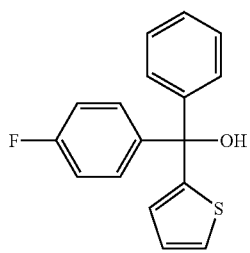

T15 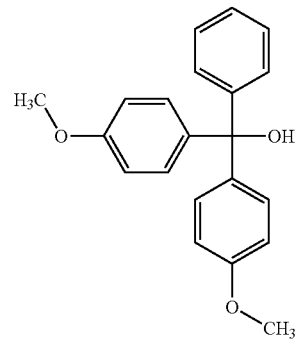
T16 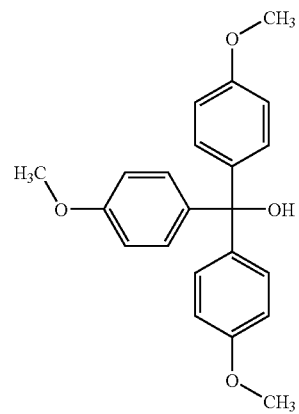
T17 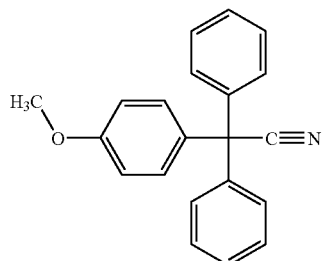
T18 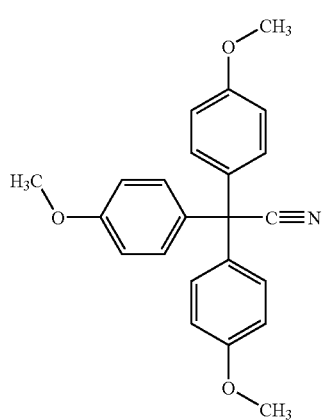
T19 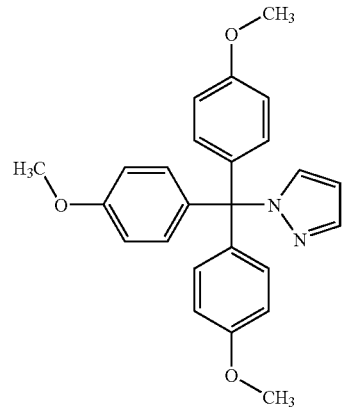
T20 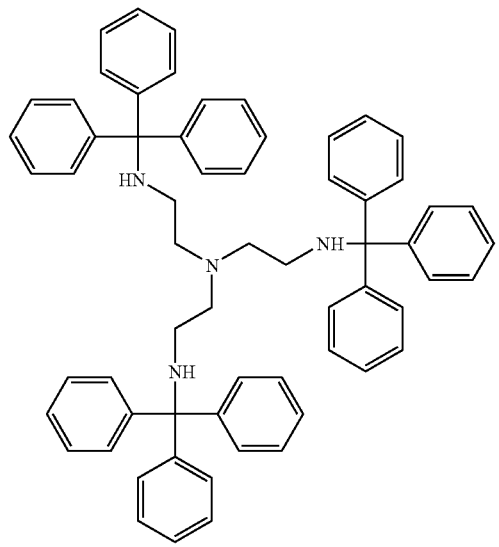
T21 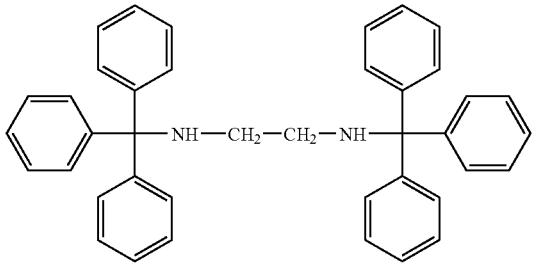
T22 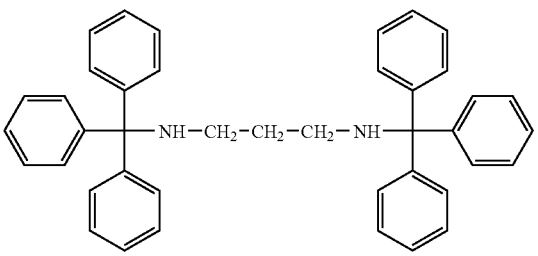

-continued
T23
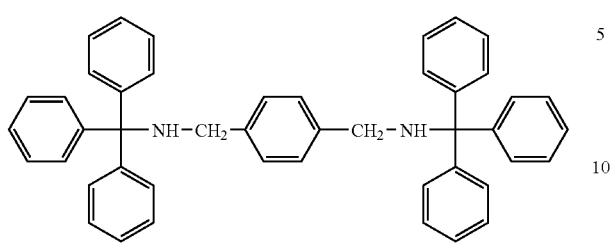
T24
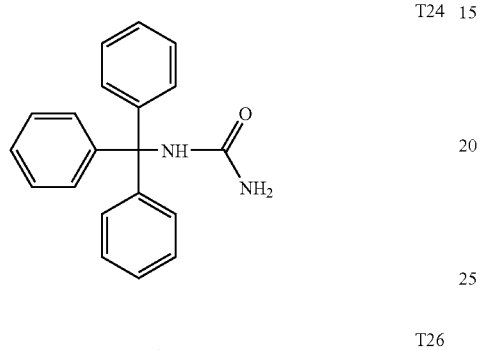
T26
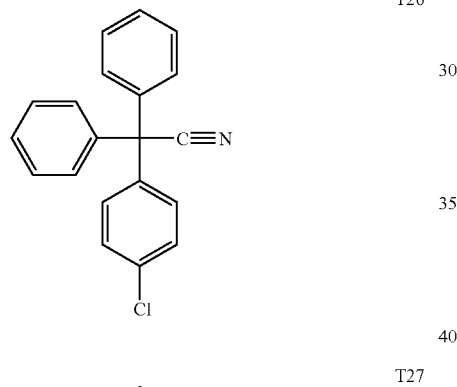
T27
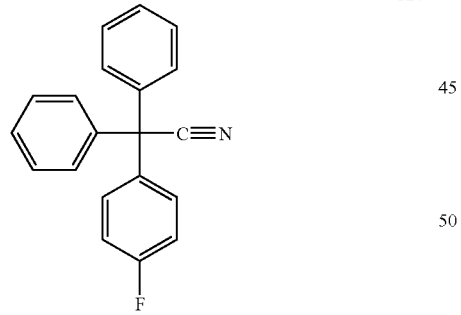
T28
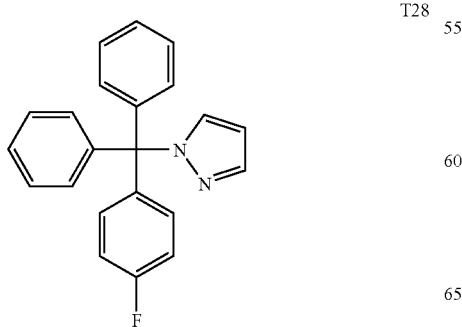
-continued
T29
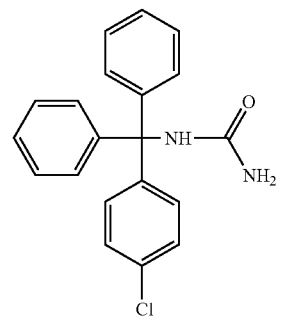
T30
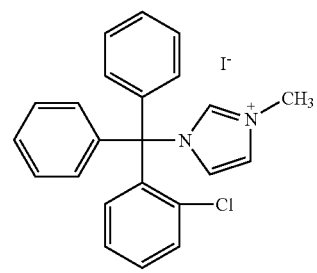
T31
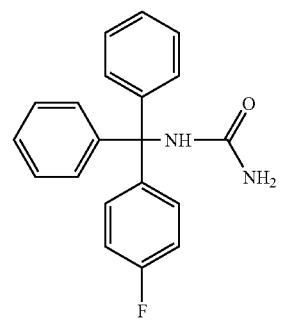
T32
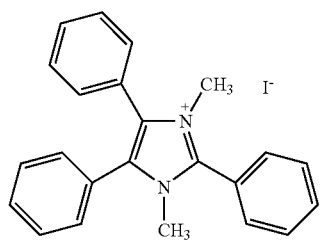
T33
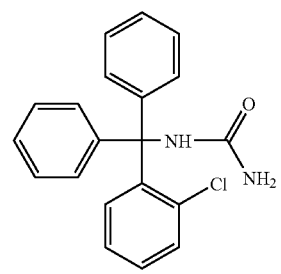

T34
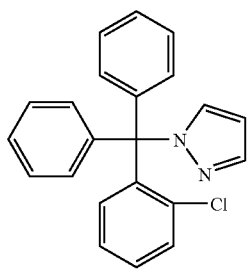
T35
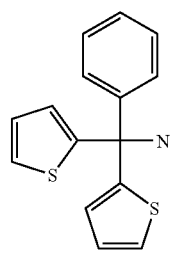
T36
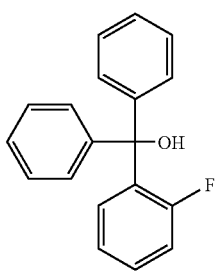
T37
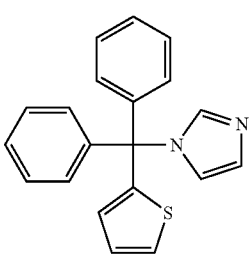
T38
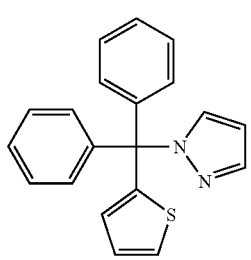
T39
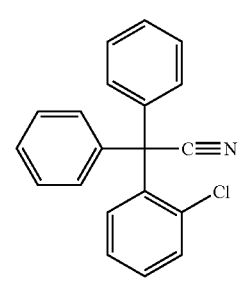
T40
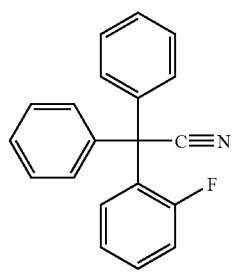
T41
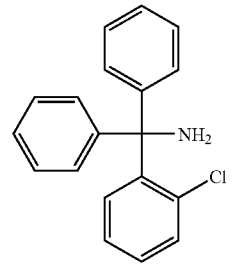
T42
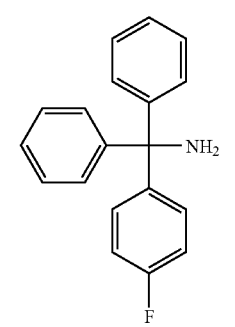
T43
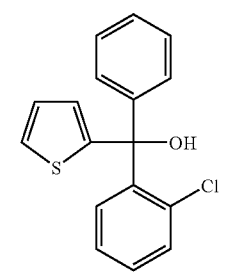
T44
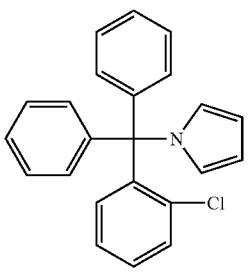

T45
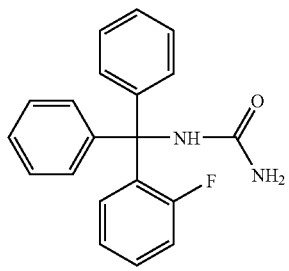
T46
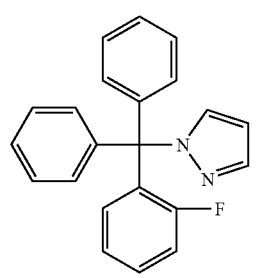
T47
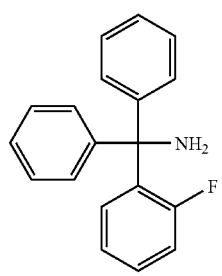
T48
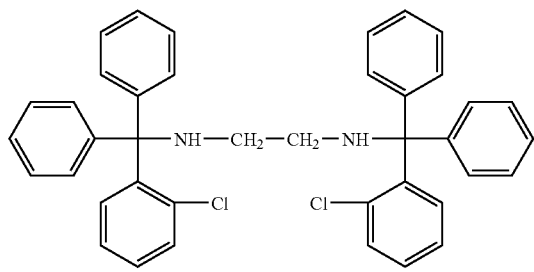
T49
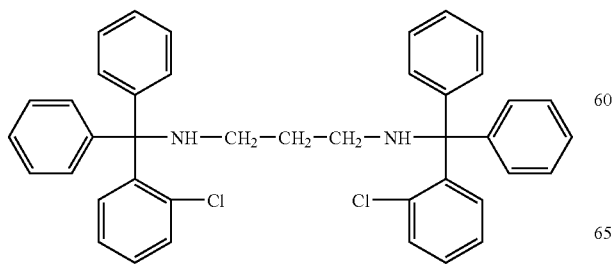
T50
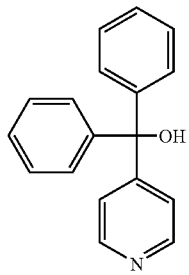
T51
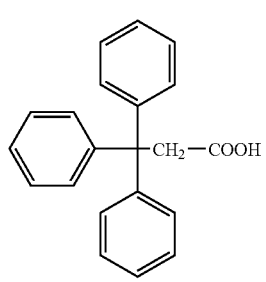
T52
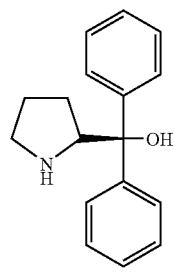
T53
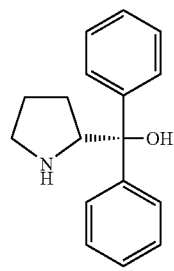
T54
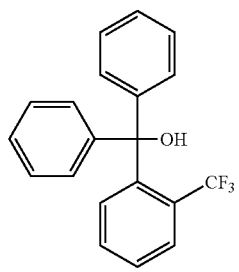

-continued
T55 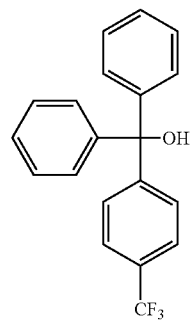
T56 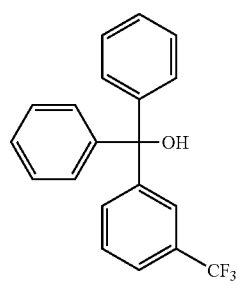
T57 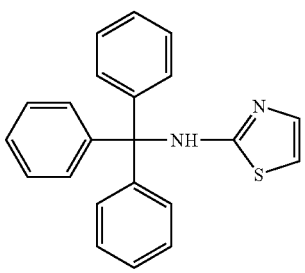
T58 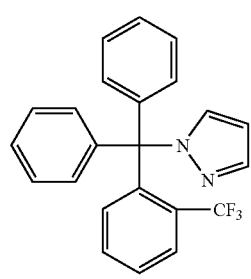
T59 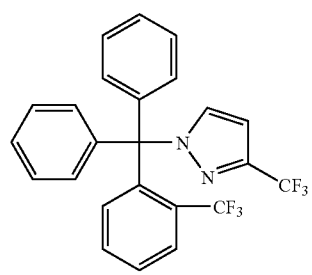
-continued
T60 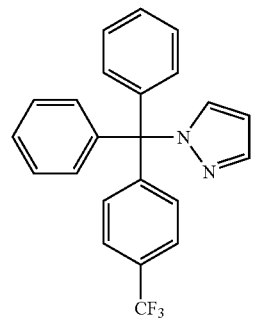
T61 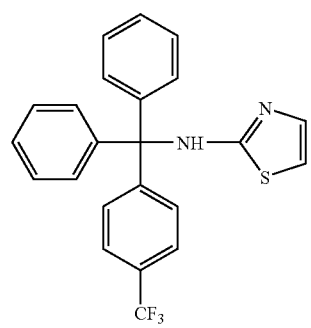
T62 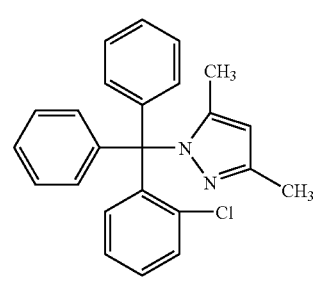
T63 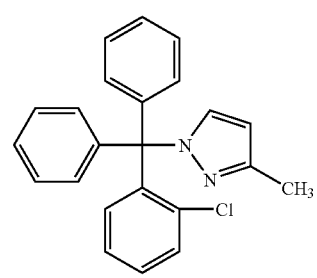
T64 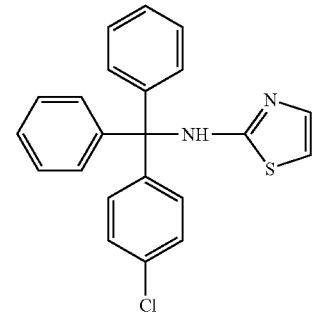

T65 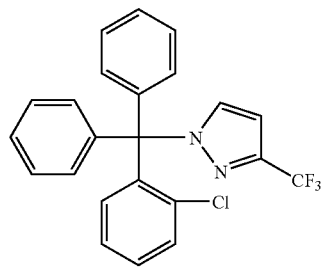
T66 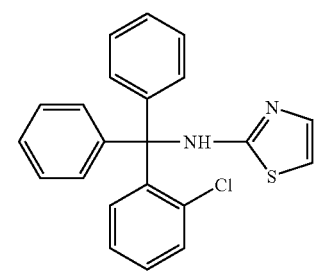
T67 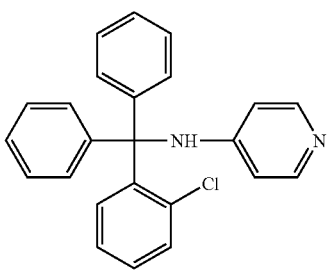
T68 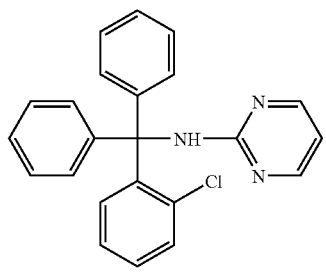
T69 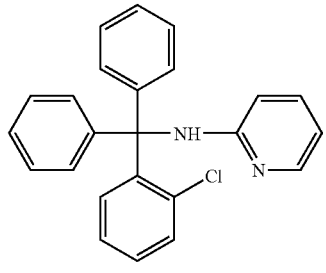
T70 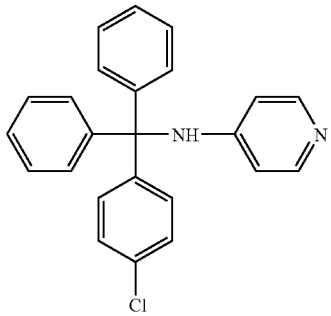
T71 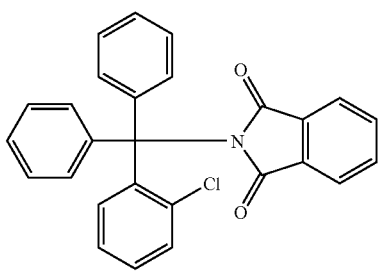
T72 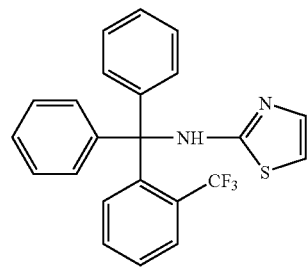
T73 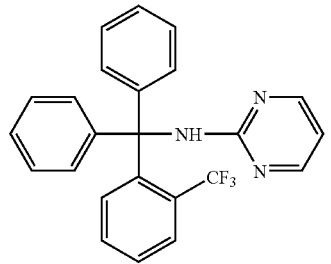
T74 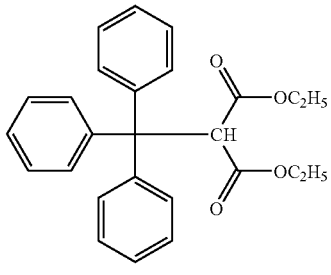

-continued
T75 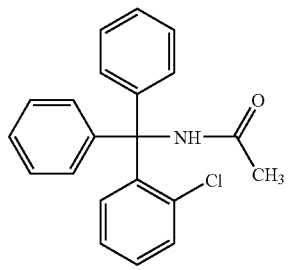
T76 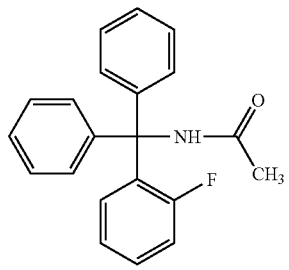
T77 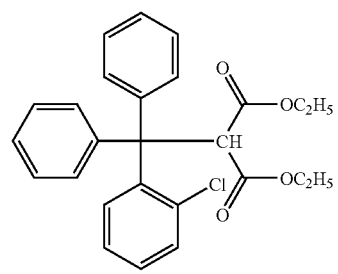
T78 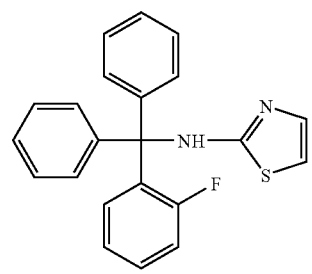
-continued
T81 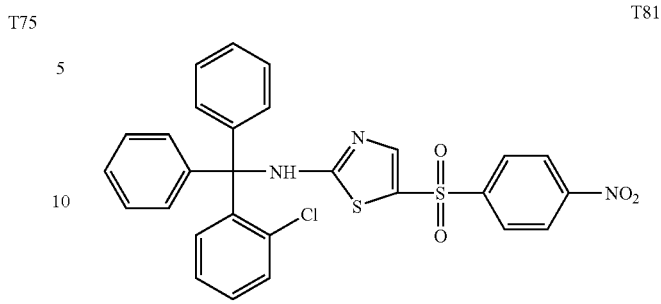
T82 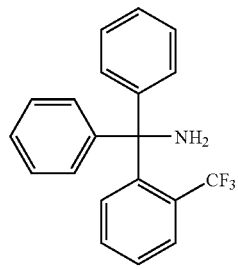
T83 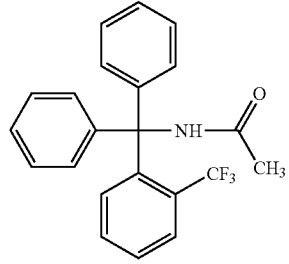
T79 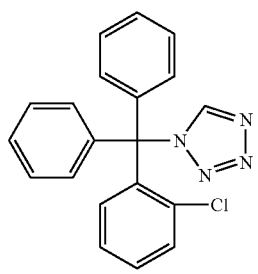

-continued

T85

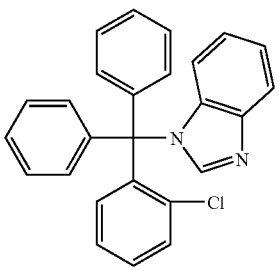

T86

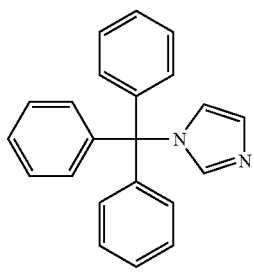

The compounds will are referred to herein by their compound numbers as given above.

We claim:

1. A method for causing inhibition of calcium activated potassium channels encoded by IKCa1 in a mammal, said method comprising the step of:

administering to the mammal, in an amount that is effective to inhibit calcium activated potassium channels encoded by IKCa1 without causing substantial inhibition of cytochrome P-450 enzymes, a triarylmethyl-1H-pyrazole compound having the formula

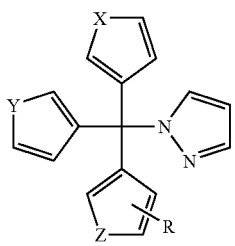

wherein:

X, Y, and Z are H—C=C—H and, wherein R is a halogen.

2. A method according to claim 1 wherein R is Fluorine.

3. A method according to claim 1 wherein R is Chlorine.

4. A method according to claim 1 wherein the compound comprises 1-[(2-chlorophenyl)diphenylmethyl]-1H-pyrazole.

5. A method according to claim 1 wherein the compound comprises 1-[(2-fluorophenyl)diphenylmethyl]-1H-pyrazole.

6. A method according to claim 1 wherein the compound comprises 1-[(4-chlorophenyl)diphenylmethyl]-1H-pyrazole.

7. A method according to claim 1 wherein the compound comprises 1-[(4-fluorophenyl)diphenylmethyl]-1H-pyrazole.

8. A method according to claim 1 wherein the compound is administered in an amount that is at least 50 times less than the amount of that compound that would cause substantial inhibition of cytochrome P-450 enzymes in the mammal.

* * * * *